United States Patent
Yoshioka et al.

(10) Patent No.: US 10,000,458 B2
(45) Date of Patent: Jun. 19, 2018

(54) PRODUCTION METHOD OF 1, 2, 4-TRIAZOLE COMPOUND

(71) Applicant: Sumitomo Chemical Company, Limited, Chuo-ku, Tokyo (JP)

(72) Inventors: Mayu Yoshioka, Tsukuba (JP); Taichi Abe, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1 day.

(21) Appl. No.: 15/471,670

(22) Filed: Mar. 28, 2017

(65) Prior Publication Data

US 2017/0283383 A1 Oct. 5, 2017

(30) Foreign Application Priority Data

Mar. 31, 2016 (JP) .................. 2016-071405

(51) Int. Cl.
*C07D 249/08* (2006.01)
(52) U.S. Cl.
CPC .................. *C07D 249/08* (2013.01)
(58) Field of Classification Search
None
See application file for complete search history.

(56) References Cited

U.S. PATENT DOCUMENTS

2015/0349267 A1   12/2015   Vo et al.

OTHER PUBLICATIONS

Chen et al, "Tunable Protic Ionic Liquids as Solvent-Catalysts for Improved Synthesis of Multiply Substituted 1,2,4-Triazoles from Oxadiazoles and Organoamines," Tetrahedron, vol. 68, pp. 4813-4819 (2012).
Bechara et al, "One-Pot Synthesis of 3,4,5-Trisubstituted 1,2,4-Triazoles Via the Addition of Hydrazides to Activated Secondary Amides," Organic Letters, vol. 17, pp. 1184-1187 (2015).
Bechara et al, "One-Pot Synthesis of 3,4,5-Trisubstituted 1,2,4-Triazoles Via the Addition of Hydrazides to Activated Secondary Amides," Organic Letters, vol. 17, 80 pgs (2015) (Supplemental Information).

*Primary Examiner* — Alicia L Otton
(74) *Attorney, Agent, or Firm* — Panitch Schwarze Belisario & Nadel LLP

(57) ABSTRACT

A method for producing a 1,2,4-triazole compound involves reacting an amide compound represented by formula (2) with a hydrazide compound represented by formula (3) in a solvent in the presence of a Lewis acid and a Lewis base, thereby obtaining a 1,2,4-triazole compound represented by formula (1):

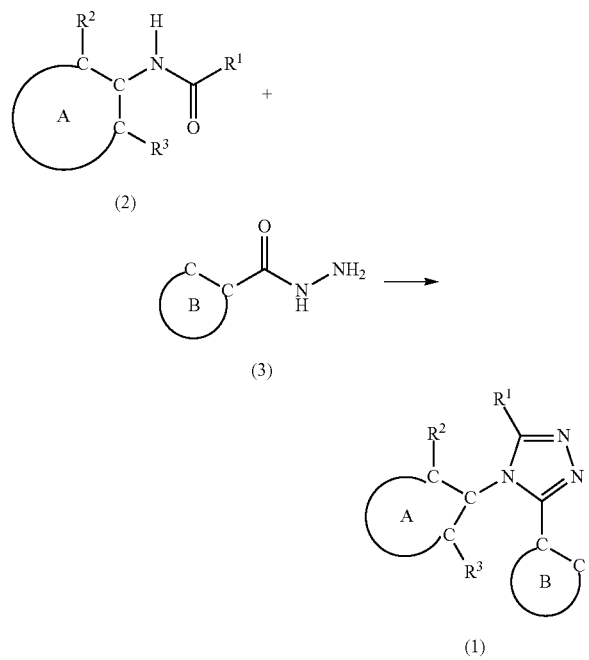

$R^1$ represents an alkyl group, a cycloalkyl group, an alkoxy group, a cycloalkoxy group, an aryl group, an aryloxy group, a monovalent heterocyclic group or a substituted amino group, $R^2$ and $R^3$ each independently represent a hydrogen atom, an alkyl group, a cycloalkyl group, an aryl group, a monovalent heterocyclic group or a substituted amino group, and Ring A and Ring B each independently represent an aromatic hydrocarbon ring or an aromatic heterocyclic ring.

8 Claims, No Drawings

PRODUCTION METHOD OF 1, 2, 4-TRIAZOLE COMPOUND

TECHNICAL FIELD

The present invention relates to a production method of a 1,2,4-triazole compound.

BACKGROUND ART

A compound having a 1,2,4-triazole ring (1,2,4-triazole compound) is useful as an intermediate of an organic electronics material. For example, Patent document 1 discloses a light emitting device using an iridium complex having a 1,2,4-triazole structure as a ligand.

For example, Patent document 1 and Non-patent document 1 disclose a synthesis method via oxadiazole as a method for synthesizing 1,2,4-triazole.

PRIOR ART DOCUMENT

Patent Document

Patent document 1: US Patent Application Publication No. 2015/0349267

Non-Patent Document

Non-Patent document 1: tetrahedron 2012,68,4813

SUMMARY OF THE INVENTION

Problem to be Solved by the Invention

The synthesis method via oxadiazole disclosed above, however, has problems of a large number of steps and low yield.

Then, the present invention has an object of providing a 1,2,4-triazole compound production method capable of obtaining a 1,2,4-triazole compound at high yield with a small number of steps.

Means for Solving the Problem

The present invention provides the following [1] to [7].

[1] A production method of a 1,2,4-triazole compound, comprising a step of reacting an amide compound represented by the formula (2) with a hydrazide compound represented by the formula (3) in a solvent in the presence of a Lewis acid and a Lewis base, thereby obtaining a 1,2,4-triazole compound represented by the formula (1):

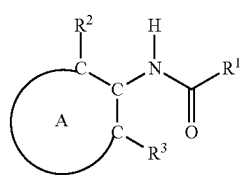

(2)

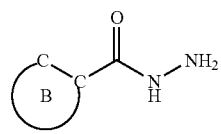

(3)

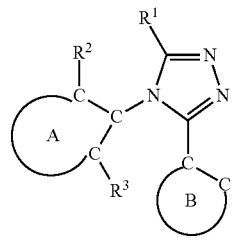

(1)

[wherein, $R^1$ represents an alkyl group, a cycloalkyl group, an alkoxy group, a cycloalkoxy group, an aryl group, an aryloxy group, a monovalent heterocyclic group or a substituted amino group, and the foregoing groups optionally have a substituent.

$R^2$ and $R^3$ each independently represent a hydrogen atom, an alkyl group, a cycloalkyl group, an aryl group, a monovalent heterocyclic group or a substituted amino group, and the foregoing groups optionally have a substituent. $R^2$ and $R^3$ may form a ring together with the carbon atoms to which they are attached and the atoms adjacent to the carbon atoms in Ring A.

Ring A and Ring B each independently represent an aromatic hydrocarbon ring or an aromatic heterocyclic ring, and the foregoing rings optionally have a substituent. When a plurality of the substituents are present, they may be the same or different and may be combined together to form a ring together with the atoms to which they are attached.].

[2] The production method according to [1],
wherein the amide compound is a compound represented by the formula (2a), and
the 1,2,4-triazole compound is a compound represented by the formula (1a):

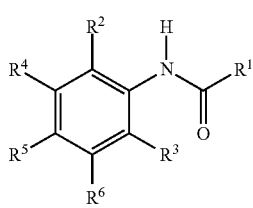

(2a)

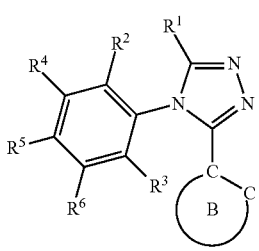

(1a)

[wherein, $R^1$, $R^2$, $R^3$ and Ring B represent the same meaning as described above.

$R^4$, $R^5$ and $R^6$ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. R² and R⁴, R⁴ and R⁵, R⁵ and R⁶, and R⁶ and R³ each may be combined together to form a ring together with the carbon atoms to which they are attached.].

[3] The production method according to [2],
wherein the hydrazide compound is a compound represented by the formula (3a), and
the 1,2,4-triazole compound is a compound represented by the formula (1b):

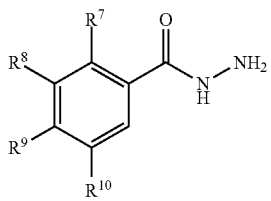
(3a)

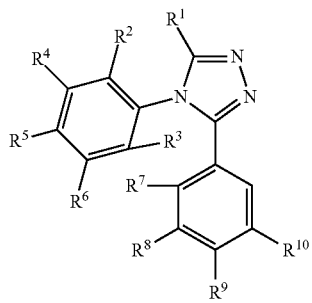
(1b)

[wherein,

R¹, R², R³, R⁴, R⁵ and R⁶ represent the same meaning as described above.

R⁷, R⁸, R⁹ and R¹⁰ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom, and the foregoing groups optionally have a substituent. R⁷ and R⁸, R⁸ and R⁹, and R⁹ and R¹⁰ each may be combined together to form a ring together with the carbon atoms to which they are attached.].

[4] The production method according to [1], wherein R¹ is an alkyl group optionally having a substituent.

[5] The production method according to [1], wherein the Lewis acid is an acid anhydride.

[6] The production method according to [1], wherein the Lewis base is an organic base.

[7] The production method according to [1], wherein the amide compound is reacted with the hydrazide compound at a temperature not higher than the boiling point of the solvent.

Effect of the Invention

According to the present invention, a 1,2,4-triazole compound production method capable of obtaining a 1,2,4-triazole compound at high yield via a small number of steps is provided.

MODES FOR CARRYING OUT THE INVENTION

Suitable embodiments of the present invention will be illustrated in detail below.
<Explanation of Common Term>
Terms commonly used in the present specification have the following meanings unless otherwise stated.

Me represents a methyl group, Et represents an ethyl group, Bu represents a butyl group, i-Pr represents an isopropyl group, t-Bu represents a tert-butyl group, and Ph represents a phenyl group.

A hydrogen atom (also written as "H") may be a heavy hydrogen atom or a light hydrogen atom.

"Alkyl group" may be any of linear or branched. The number of carbon atoms of the linear alkyl group is, not including the number of carbon atoms of a substituent, usually 1 to 50, preferably 1 to 10, more preferably 1 to 5. The number of carbon atoms of the branched alkyl groups is, not including the number of carbon atoms of a substituent, usually 3 to 50, preferably 3 to 30, more preferably 4 to 20, further preferably 5 to 10.

The alkyl group optionally has a substituent. Examples thereof include a methyl group, an ethyl group, a propyl group, an isopropyl group, a butyl group, a 2-butyl group, an isobutyl group, a tert-butyl group, a pentyl group, an isoamyl group, a 2-ethylbutyl group, a hexyl group, a heptyl group, an octyl group, a 2-ethylhexyl group, a 3-propylheptyl group, a decyl group, a 3,7-dimethyloctyl group, a 2-ethyloctyl group, a 2-hexyldecyl group, a dodecyl group and the like. The alkyl groups may be groups obtained by substituting a part or all of hydrogen atoms in these groups with a cycloalkyl group, an alkoxy group, a cycloalkoxy group, an aryl group, a fluorine atom or the like. Examples thereof include a trifluoromethyl group, a pentafluoroethyl group, a perfluorobutyl group, a perfluorohexyl group, a perfluorooctyl group, a 3-phenylpropyl group, a 3-(4-methylphenyl) propyl group, a 3-(3,5-di-hexylphenyl) propyl group and a 6-ethyloxyhexyl group.

The number of carbon atoms of "Cycloalkyl group" is, not including the number of carbon atoms of a substituent, usually 3 to 50, preferably 3 to 30, more preferably 4 to 20.

The cycloalkyl group optionally has a substituent. Examples thereof include a cyclohexyl group, a cyclohexylmethyl group and a cyclohexylethyl group.

"Aryl group" denotes an atomic group remaining after removing from an aromatic hydrocarbon one hydrogen atom linked directly to a carbon atom constituting the ring. The number of carbon atoms of the aryl group is, not including the number of carbon atoms of a substituent, usually 6 to 60, preferably 6 to 20, more preferably 6 to 10.

The aryl group optionally has a substituent. Examples thereof include a phenyl group, a 1-naphthyl group, a 2-naphthyl group, a 1-anthracenyl group, a 2-anthracenyl group, a 9-anthracenyl group, a 1-pyrenyl group, a 2-pyrenyl group, a 4-pyrenyl group, a 2-fluorenyl group, a 3-fluorenyl group, a 4-fluorenyl group, a 2-phenylphenyl group, a 3-phenylphenyl group, a 4-phenylphenyl group and the like. The aryl groups may be groups obtained by substituting a part or all of hydrogen atoms in these groups with an alkyl group, a cycloalkyl group, an alkoxy group, a cycloalkoxy group, an aryl group, a fluorine atom or the like.

"Alkoxy group" may be any of linear or branched. The number of carbon atoms of the linear alkoxy group is, not including the number of carbon atoms of a substituent, usually 1 to 40, preferably 4 to 10. The number of carbon atoms of the branched alkoxy group is, not including the number of carbon atoms of a substituent, usually 3 to 40, preferably 4 to 10.

The alkoxy group optionally has a substituent. Examples thereof include a methoxy group, an ethoxy group, a propyloxy group, an isopropyloxy group, a butyloxy group, an isobutyloxy group, a tert-butyloxy group, a pentyloxy group, a hexyloxy group, a heptyloxy group, an octyloxy group, a 2-ethylhexyloxy group, a nonyloxy group, a decyloxy group, a 3,7-dimethyloctyloxy group, a lauryloxy group and the like. The alkoxy groups may be groups obtained by substituting a part or all of hydrogen atoms in these groups with a cycloalkyl group, an alkoxy group, a cycloalkoxy group, an aryl group, a fluorine atom or the like.

The number of carbon atoms of "Cycloalkoxy group" is, not including the number of carbon atoms of a substituent, usually 3 to 40, preferably 4 to 10.

The cycloalkoxy group optionally has a substituent. Examples thereof include a cyclohexyloxy group.

The number of carbon atoms of "Aryloxy group" is, not including the number of carbon atoms of a substituent, usually 6 to 60, preferably 6 to 48.

The aryloxy group optionally has a substituent. Examples thereof include a phenoxy group, a 1-naphthyloxy group, 2-naphthyloxy group, a 1-anthracenyloxy group, a 9-anthracenyloxy group, a 1-pyrenyloxy group and the like. The aryloxy groups may be groups obtained by substituting a part or all of hydrogen atoms in these groups with an alkyl group, a cycloalkyl group, an alkoxy group, a cycloalkoxy group, a fluorine atom or the like.

"p-Valent heterocyclic group" (p represents an integer of 1 or more) denotes an atomic group remaining after removing from a heterocyclic compound p hydrogen atoms among hydrogen atoms directly linked to a carbon atom or a hetero atom constituting the ring. Of p-valent heterocyclic groups, "p-valent aromatic heterocyclic groups" as an atomic group remaining after removing from an aromatic heterocyclic compound p hydrogen atoms among hydrogen atoms directly linked to a carbon atom or a hetero atom constituting the ring are preferable.

"Aromatic heterocyclic compound" denotes a compound in which the heterocyclic ring itself shows aromaticity such as oxadiazole, thiadiazole, thiazole, oxazole, thiophene, pyrrole, phosphole, furan, pyridine, pyrazine, pyrimidine, triazine, pyridazine, quinoline, isoquinoline, carbazole and dibenzophosphole, and a compound in which an aromatic ring is condensed to the heterocyclic ring even if the heterocyclic ring itself shows no aromaticity such as phenoxazine, phenothiazine, dibenzoborole, dibenzosilole and benzopyran.

The number of carbon atoms of the p-Valent heterocyclic group is, not including the number of carbon atoms of a substituent, usually 2 to 60, preferably 3 to 20, more preferably 4 to 20.

The p-Valent heterocyclic group optionally has a substituent. Examples of the monovalent heterocyclic group of the p-Valent heterocyclic group include a thienyl group, pyrrolyl group, a furyl group, a pyridyl group, a piperidyl group, a quinolinyl group, an isoquinolinyl group, a pyrimidinyl group, a triazinyl group and the like. The monovalent heterocyclic groups may be groups obtained by substituting a part or all of hydrogen atoms in these groups with an alkyl group, a cycloalkyl group, an alkoxy group, a cycloalkoxy group or the like.

"Halogen atom" denotes a fluorine atom, a chlorine atom, a bromine atom or an iodine atom.

"Amino group" optionally has a substituent, and a substituted amino group is preferable. The substituent which an amino group has is preferably an alkyl group, a cycloalkyl group, an aryl group or a monovalent heterocyclic group.

The substituted amino group is preferably a disubstituted amino group. The disubstituted amino group includes, for example, a dialkylamino group, a dicycloalkylamino group and a diarylamino group.

Examples of the disubstituted amino group include, for example, a dimethylamino group, a diethylamino group, a diphenylamino group, a bis(4-methylphenyl)amino group, bis(4-tert-butylphenyl)amino group and a bis(3,5-di-tert-butylphenyl)amino group.

"Alkenyl group" may be any of linear or branched. The number of carbon atoms of the linear alkenyl group, not including the number of carbon atoms of the substituent, is usually 2 to 30, preferably 3 to 20. The number of carbon atoms of the branched alkenyl group, not including the number of carbon atoms of the substituent, is usually 3 to 30, preferably 4 to 20.

The number of carbon atoms of "Cycloalkenyl group", not including the number of carbon atoms of the substituent, is usually 3 to 30, preferably 4 to 20.

The alkenyl group and cycloalkenyl group optionally have a substituent. Examples of the alkenyl group include, for example, a vinyl group, a 1-propenyl group, a 2-propenyl group, a 2-butenyl group, a 3-butenyl group, a 3-pentenyl group, 4-pentenyl group, a 1-hexenyl group, a 5-hexenyl group, a 7-octenyl group, and groups obtained by substituting a part or all of hydrogen atoms in these groups with a substitutent. Examples of the cycloalkenyl group include, for example, cyclohexenyl group and 2-norbornylenyl group.

"Alkynyl group" may be any of linear or branched. The number of carbon atoms of the alkynyl group, not including the number of carbon atoms of the substituent, is usually 2 to 20, preferably 3 to 20. The number of carbon atoms of the branched alkynyl group, not including the number of carbon atoms of the substituent, is usually 4 to 30, preferably 4 to 20.

The number of carbon atoms of "Cycloalkynyl group", not including the number of carbon atoms of the substituent, is usually 4 to 30, preferably 4 to 20.

The alkynyl group and cycloalkynyl group optionally have a substituent. Examples of the alkynyl group include, for example, an ethynyl group, a 1-propynyl group, a 2-propynyl group, a 2-butynyl group, a 3-butynyl group, a 3-pentynyl group, a 4-pentynyl group, a 1-hexynyl group, a 5-hexynyl group, and groups obtained by substituting a part or all of hydrogen atoms in these groups with a substitutent.

"Arylene group" denotes an atomic group remaining after removing from an aromatic hydrocarbon two hydrogen atoms linked directly to carbon atoms constituting the ring. The number of carbon atoms of the arylene group is, not including the number of carbon atoms of a substituent, usually 6 to 60, preferably 6 to 30, more preferably 6 to 18.

The arylene group optionally has a substituent. Examples thereof include a phenylene group, a naphthalenediyl group, an anthracenediyl group, a phenanthrenediyl group, a dihydrophenanthrenediyl group, a naphthacenediyl group, a fluorenediyl group, a pyrenediyl group, a perylenediyl group, a chrysenediyl group, and groups obtained by substituting a part or all of hydrogen atoms in these groups with a substitutent. The arylene group is preferably groups represented by the formulae (A-1) to (A-20). The arylene group includes groups obtained by linking a plurality of these groups.

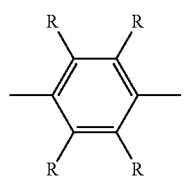 (A-1)
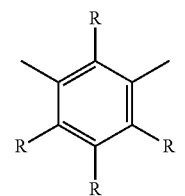 (A-2)
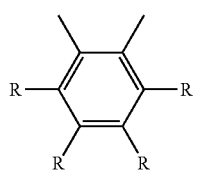 (A-3)
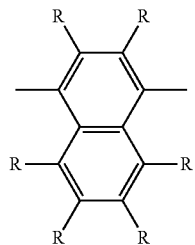 (A-4)
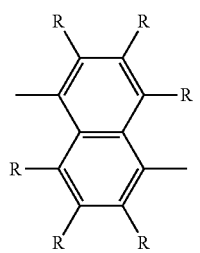 (A-5)
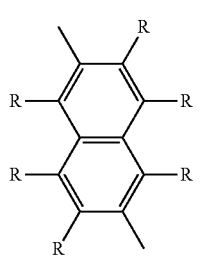 (A-6)
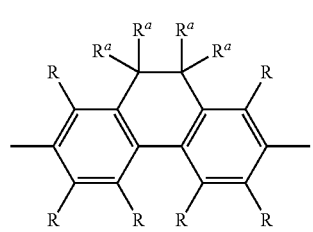 (A-7)
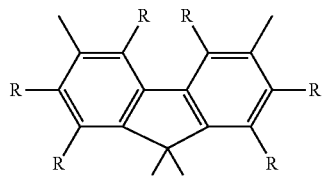 (A-8)
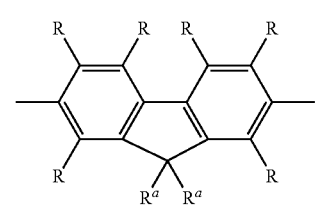 (A-9)
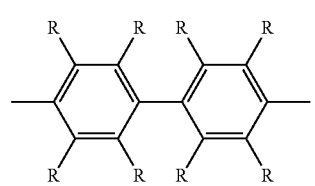 (A-10)
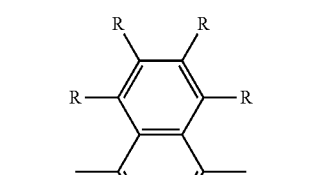 (A-11)
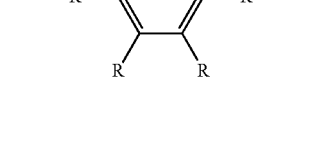 (A-12)
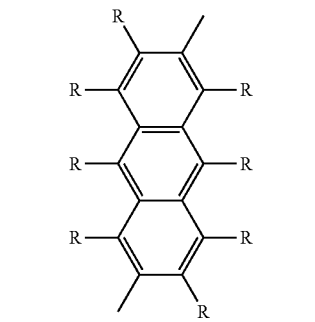 (A-13)

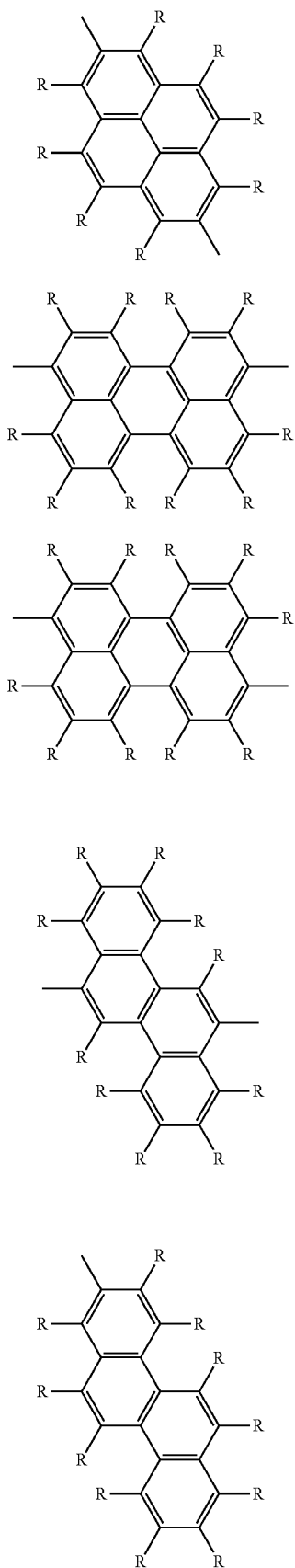

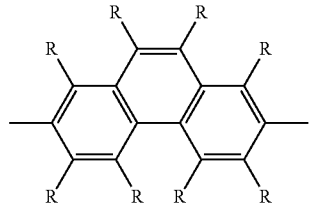
(A-14)

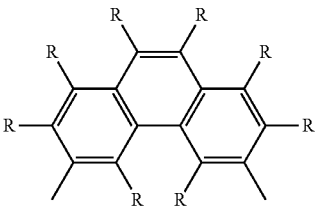
(A-19)

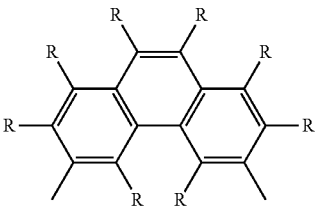
(A-20)

In the formulae, R and $R^a$ each independently represent a hydrogen atom, an alkyl group, a cycloalkyl group, an aryl group or a monovalent heterocyclic group. The plurality of R and $R^a$ each may be the same or different, and groups $R^a$ may be combined together to form a ring together with the atoms to which they are attached.

The number of carbon atoms of the divalent heterocyclic group is, not including the number of carbon atoms of a substituent, usually 2 to 60, preferably 3 to 20, more preferably 4 to 15.

The divalent heterocyclic group optionally has a substituent. Examples thereof include, for example, divalent groups obtained by removing from pyridine, diazabenzene, triazine, azanaphthalene, diazanaphthalene, carbazole, dibenzofuran, dibenzothiophene, dibenzosilole, phenoxazine, phenothiazine, acridine, dihydroacridine, furan, thiophene, azole, diazole and triazole two hydrogen atoms among hydrogen atoms linking directly to a carbon atom or a hetero atom constituting the ring, and groups obtained by substituting a part or all of hydrogen atoms in these groups with a substitutent. The divalent heterocyclic group is preferably groups represented by the formulae (AA-1) to (AA-34). The divalent heterocyclic group includes groups obtained by linking a plurality of these groups.

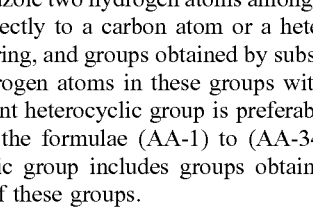
(AA-1)

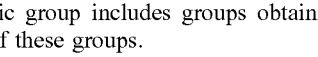
(AA-2)

-continued
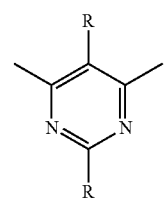
(AA-3)
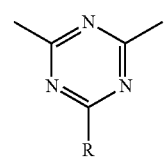
(AA-4)
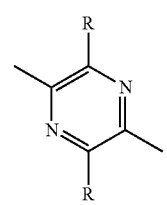
(AA-5)
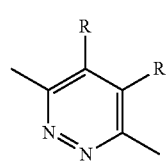
(AA-6)
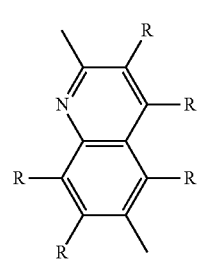
(AA-7)
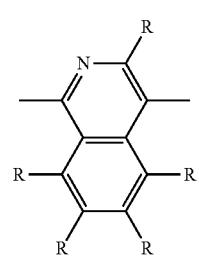
(AA-8)
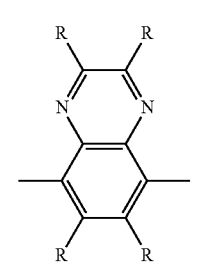
(AA-9)
-continued
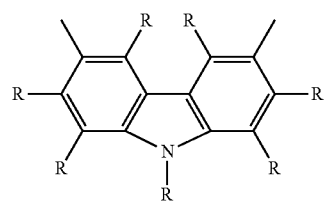
(AA-10)
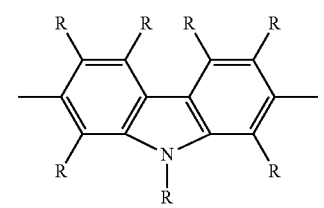
(AA-11)
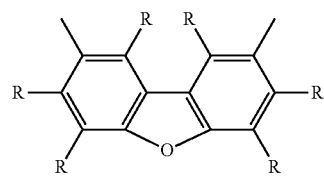
(AA-12)
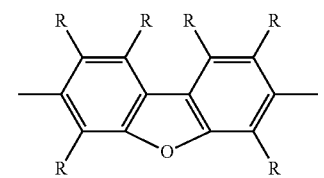
(AA-13)
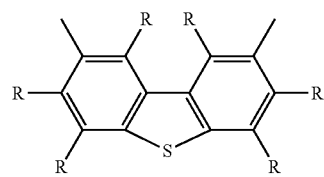
(AA-14)
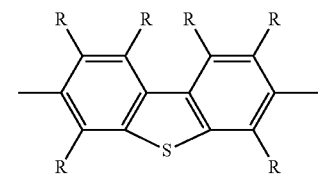
(AA-15)
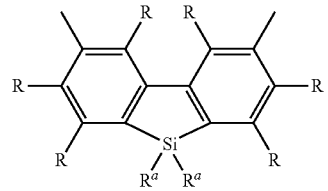
(AA-16)
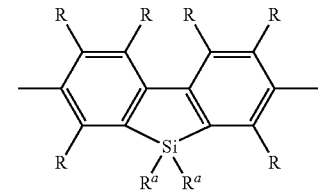
(AA-17)

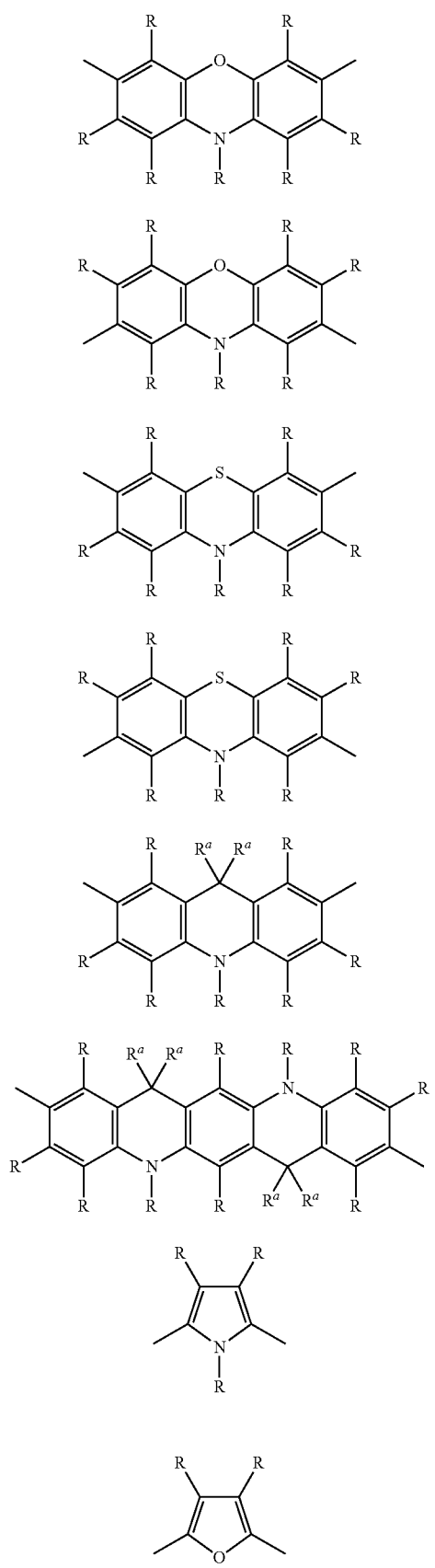
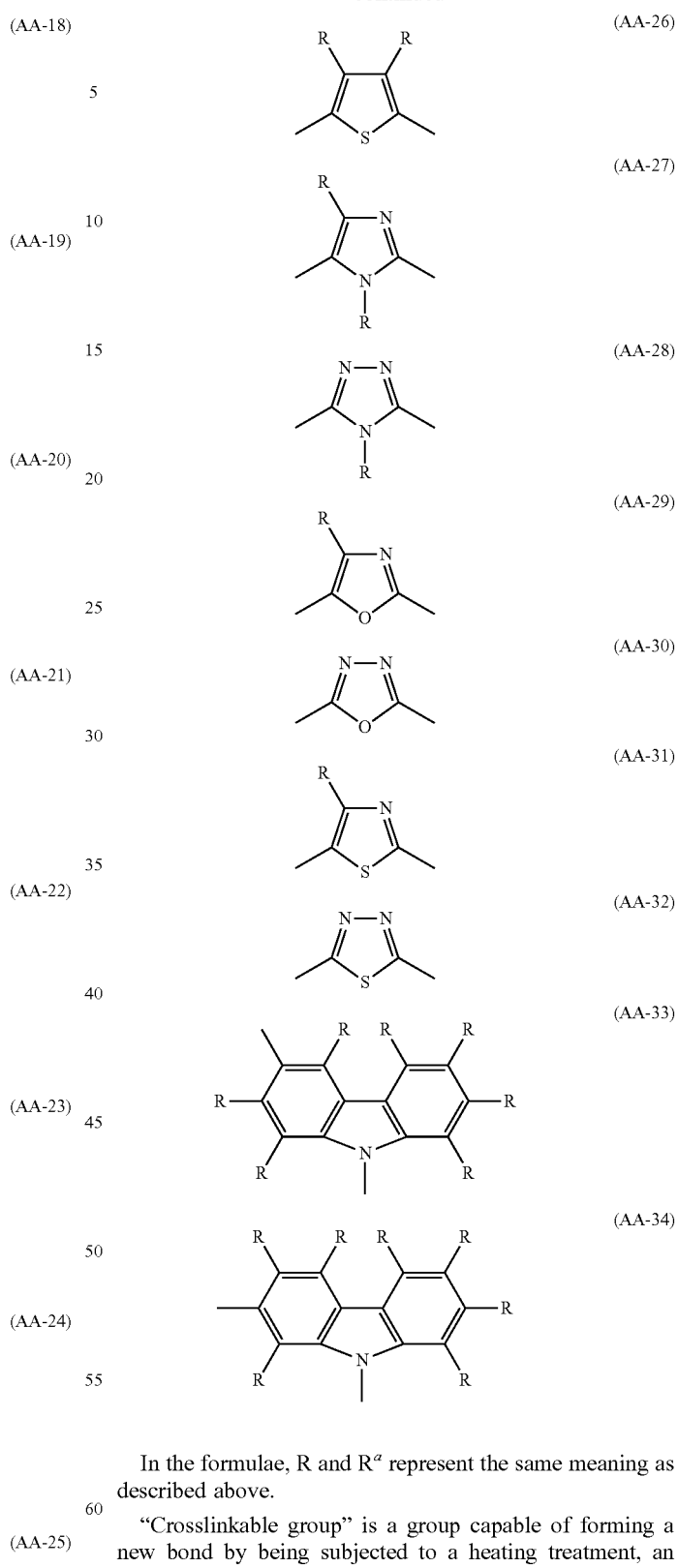

In the formulae, R and $R^a$ represent the same meaning as described above.

"Crosslinkable group" is a group capable of forming a new bond by being subjected to a heating treatment, an ultraviolet irradiation treatment, a near-ultraviolet irradiation treatment, a visible light irradiation treatment, a radical reaction and the like. The crosslinkable group is preferably any one of groups represented by the formulae (B-1) to (B-17). These groups optionally have a substituent.

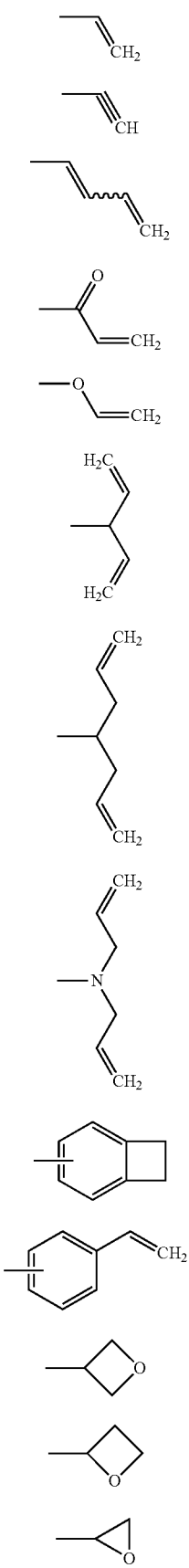

(B-1)
(B-2)
(B-3)
(B-4)
(B-5)
(B-6)
(B-7)
(B-8)
(B-9)
(B-10)
(B-11)
(B-12)
(B-13)
(B-14)
(B-15)
(B-16)
(B-17)

"Substituent" represents a halogen atom, a cyano group, an alkyl group, a cycloalkyl group, an aryl group, a monovalent heterocyclic group, an alkoxy group, a cycloalkoxy group, an aryloxy group, an amino group, a substituted amino group, an alkenyl group, a cycloalkenyl group, an alkynyl group or a cycloalkynyl group. The substituent may be a crosslinkable group.

In the present specification, an aryl group, a monovalent heterocyclic group or a substituted amino group may be a dendron.

"Dendron" is a group having a regular dendritic branched structure having a branching point at an atom or ring (that is, a dendrimer structure). A compound having a dendron (hereinafter, referred to as "dendrimer".) includes, for example, structures described in literatures such as International Publication WO 02/067343, JP-A No. 2003-231692, International Publication WO 2003/079736 and international Publication WO 2006/097717.

The dendron is preferably a group represented by the formula (D-A) or (D-B).

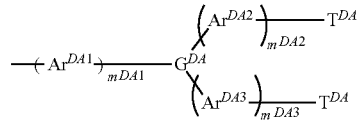
(D-A)

In the formula, $m^{DA1}$, $m^{DA2}$ and $m^{DA3}$ each independently represent an integer of 0 or more.

$G^{DA}$ represents a nitrogen atom, an aromatic hydrocarbon group or a heterocyclic group, and the foregoing groups optionally have a substituent.

$Ar^{DA1}$, $Ar^{DA2}$ and $Ar^{DA3}$ each independently represent an arylene group or a divalent heterocyclic group, and the foregoing groups optionally have a substituent. When a plurality of $Ar^{DA1}$, $Ar^{DA2}$ and $Ar^{DA3}$ are present, they may be the same or different at each occurrence.

$T^{DA}$ represents an aryl group or a monovalent heterocyclic group, and the foregoing groups optionally have a substituent. The plurality of $T^{DA}$ may be the same or different.

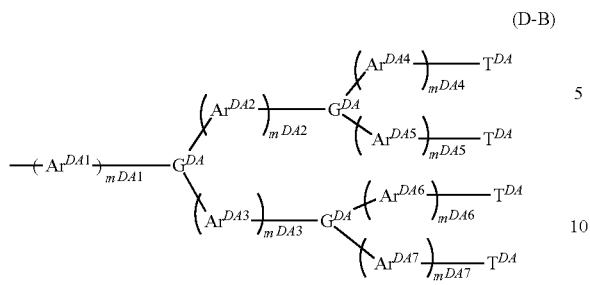

(D-B)

In the formula, $m^{DA1}$, $m^{DA2}$, $m^{DA3}$, $m^{DA4}$, $m^{DA5}$, $m^{DA6}$ and $m^{DA7}$ each independently represent an integer of 0 or more.

$G^{DA}$ represents a nitrogen atom, an aromatic hydrocarbon group or a heterocyclic group, and the foregoing groups optionally have a substituent. The plurality of $G^{DA}$ may be the same or different.

$Ar^{DA1}$, $Ar^{DA2}$, $Ar^{DA3}$, $Ar^{DA4}$, $Ar^{DA5}$, $Ar^{DA6}$ and $Ar^{DA7}$ each independently represent an arylene group or a divalent heterocyclic group, and the foregoing groups optionally have a substituent. When a plurality of $Ar^{DA1}$, $Ar^{DA2}$, $Ar^{DA3}$, $Ar^{DA4}$, $Ar^{DA5}$, $Ar^{DA6}$ and $Ar^{DA7}$ are present, they may be the same or different at each occurrence.

$T^{DA}$ represents an aryl group or a monovalent heterocyclic group, and the foregoing groups optionally have a substituent. The plurality of $T^{DA}$ may be the same or different.

$m^{DA1}$, $m^{DA2}$, $m^{DA3}$, $m^{DA4}$, $m^{DA5}$, $m^{DA6}$ and $m^{DA7}$ are usually an integer of 10 or less, preferably an integer of 5 or less, more preferably 0 or 1. It is preferable that $m^{DA2}$, $m^{DA3}$, $m^{DA4}$, $m^{DA5}$, $m^{DA6}$ and $m^{DA7}$ are the same integer, and it is more preferable that $m^{DA1}$, $m^{DA2}$, $m^{DA3}$, $m^{DA4}$, $m^{DA5}$, $m^{DA6}$ and $m^{DA7}$ are the same integer, and it is further preferable that $m^{DA1}$, $m^{DA2}$, $m^{DA3}$, $m^{DA4}$, $m^{DA5}$, $m^{DA6}$ and $m^{DA7}$ are 0.

$G^{DA}$ is preferably a group represented by the formula (GDA-11) to (GDA-15), and the foregoing groups optionally have a substituent.

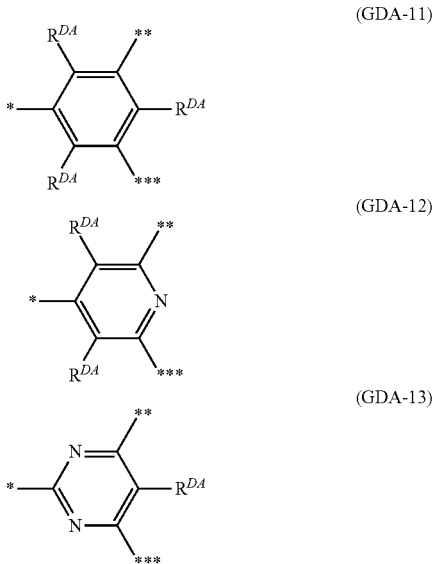

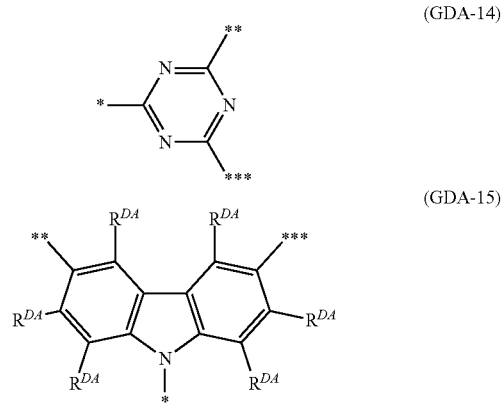

In the formulae,

* represents a linkage to $Ar^{DA1}$ in the formula (D-A), $Ar^{DA1}$ in the formula (D-B), $Ar^{DA2}$ in the formula (D-B) or $Ar^{DA3}$ in the formula (D-B).

** represents a linkage to $Ar^{DA2}$ in the formula (D-A), $Ar^{DA2}$ in the formula (D-B), $Ar^{DA4}$ in the formula (D-B) or $Ar^{DA6}$ in the formula (D-B).

*** represents a linkage to $Ar^{DA3}$ in the formula (D-A), $Ar^{DA3}$ in the formula (D-B), $Ar^{DA5}$ in the formula (D-B) or $Ar^{DA7}$ in the formula (D-B).

$R^{DA}$ represents a hydrogen atom, an alkyl group, a cycloalkyl group, an alkoxy group, a cycloalkoxy group, an aryl group or a monovalent heterocyclic group, and the foregoing groups optionally have a substituent. When a plurality of $R^{DA}$ are present, they may be the same or different.

$R^{DA}$ is preferably a hydrogen atom, an alkyl group, a cycloalkyl group, an alkoxy group or a cycloalkoxy group, more preferably a hydrogen atom, an alkyl group or cycloalkyl group, and the foregoing groups optionally have a substituent.

It is preferable that $Ar^{DA1}$, $Ar^{DA2}$, $Ar^{DA3}$, $Ar^{DA4}$, $Ar^{DA5}$, $Ar^{DA6}$ and $Ar^{DA7}$ are groups represented by the formulae (ArDA-1) to (ArDA-3).

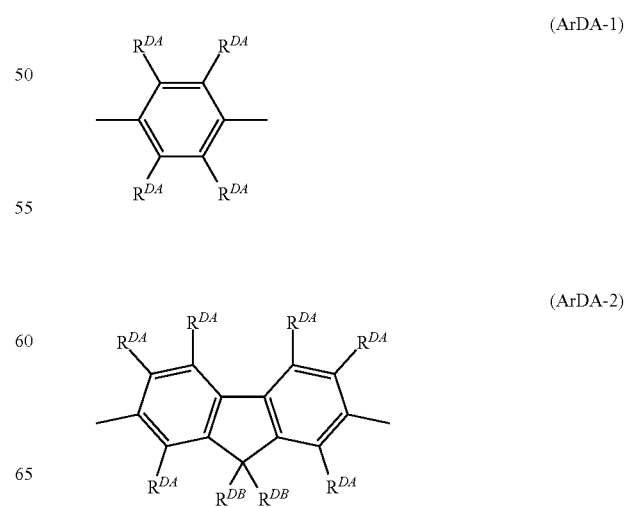

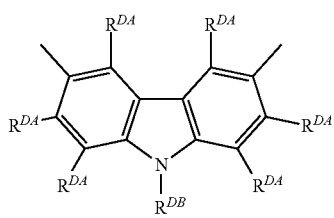
(ArDA-3)

In the formulae, $R^{DA}$ represents the same meaning as described above.

$R^{DB}$ represents a hydrogen atom, an alkyl group, a cycloalkyl group, an aryl group or a monovalent heterocyclic group, and the foregoing groups optionally have a substituent. When a plurality of $R^{DB}$ are present, they may be the same or different at each occurrence.

$R^{DB}$ is preferably an alkyl group, a cycloalkyl group, an aryl group or a monovalent heterocyclic group, more preferably an aryl group or a monovalent heterocyclic group, further preferably an aryl group, and the foregoing groups optionally have a substituent.

$T^{DA}$ is preferably groups represented by the formulae (TDA-1) to (TDA-3).

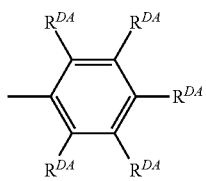
(TDA-1)

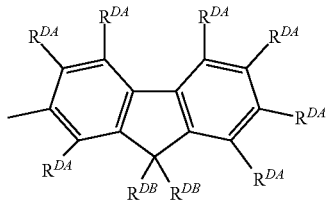
(TDA-2)

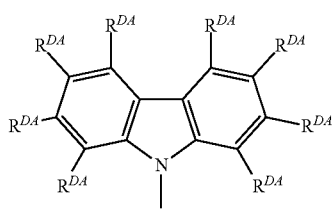
(TDA-3)

In the formulae, $R^{DA}$ and $R^{DB}$ represent the same meaning described above.

The group represented by the formula (D-A) is preferably a group represented by the formula (D-A1) to (D-A3).

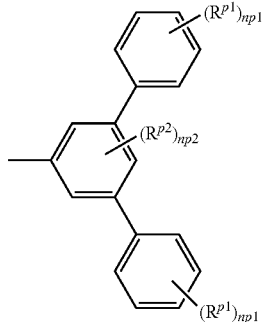
(D-A1)

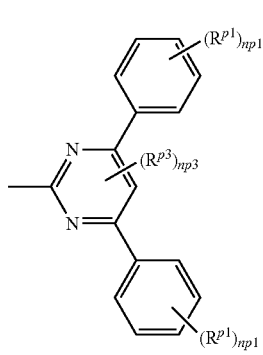
(D-A2)

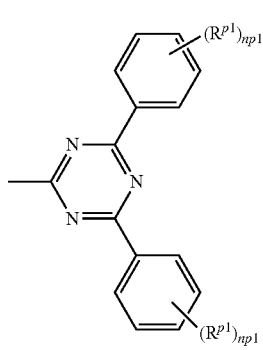
(D-A3)

In the formulae, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. The plurality of np1 may be the same or different.

The group represented by the formula (D-B) is preferably a group represented by the formula (D-B1) to (D-B3).

(D-B1)

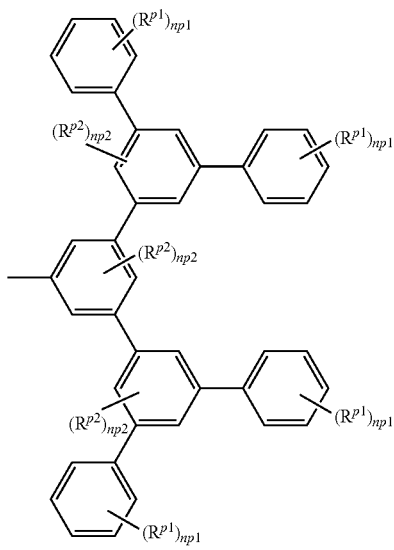

(D-B3)

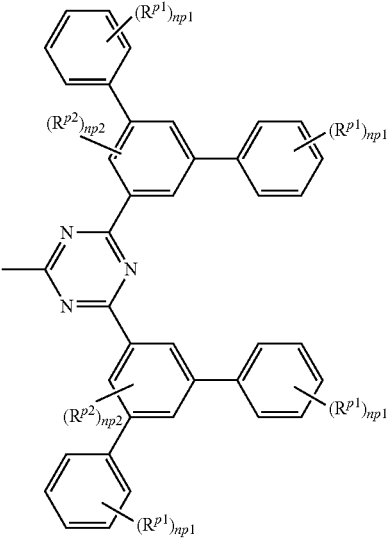

(D-B2)

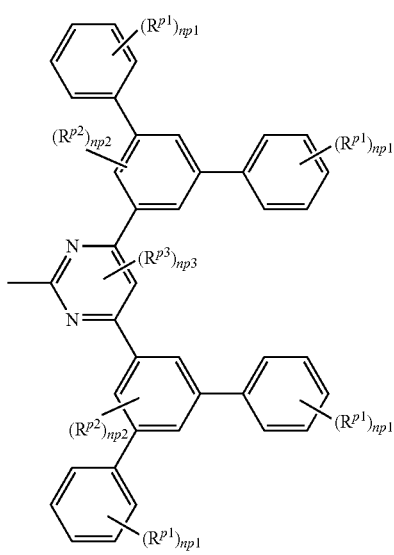

In the formulae, $R^{p1}$, $R^{p2}$ and $R^{p3}$ each independently represent an alkyl group, a cycloalkyl group, an alkoxy group, a cycloalkoxy group or a halogen atom. When a plurality of $R^{p1}$ and $R^{p2}$ are present, they may be the same or different at each occurrence.

np1 represents an integer of 0 to 5, np2 represents an integer of 0 to 3, and np3 represents 0 or 1. When a plurality of np1 and np2 are present, they may be the same or different at each occurrence.

np1 is preferably an integer of 0 to 3, more preferably an integer of 1 to 3, further preferably 1. np2 is preferably 0 or 1, more preferably 0. np3 is preferably 0.

$R^{p1}$, $R^{p2}$ and $R^{p3}$ are preferably an alkyl group or a cycloalkyl group.

<Production Method of 1,2,4-triazole Compound>

The production method according to the present embodiment comprises a step of reacting an amide compound represented by the formula (2) with a hydrazide compound represented by the formula (3) in a solvent in the presence of a Lewis acid and a Lewis base, thereby obtaining a 1,2,4-triazole compound represented by the formula (1).

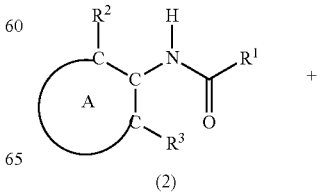

(2)

$R^1$ is preferably an alkyl group, a cycloalkyl group, an aryl group or a monovalent heterocyclic group, more preferably an alkyl group, a cycloalkyl group or an aryl group, further preferably an alkyl group or an aryl group, particularly preferably an alkyl group, and the foregoing groups optionally have a substituent. $R^1$ is especially preferably an alkyl group having no substituent.

$R^1$ may be, for example, a linear alkyl group, and suitable examples of the linear alkyl group represented by $R^1$ include a methyl group, an ethyl group, a n-propyl group, a n-butyl group, a n-hexyl group, a n-heptyl group, a n-octyl group and the like.

$R^1$ may be, for example, a branched alkyl group, and suitable examples of the branched alkyl group represented by $R^1$ include groups represented by the formulae (I-01) to (I-21), and groups represented by the formulae (I-08) to (I-10) or the formulae (I-12) to (I-15) are preferable, groups represented by the formulae (I-08) to (I-10), the formula (I-12) or the formula (I-13) are more preferable.

R¹ may be, for example, a cycloalkyl group, and suitable examples of the cycloalkyl group represented by R¹ include a cyclopentyl group, a cyclohexyl group and the like.

R¹ may be, for example, an aryl group, and suitable examples of the aryl group represented by R¹ include groups represented by the formulae (IV-01) to (IV-09), groups represented by the formulae (V-01) to (V-08) and the like.

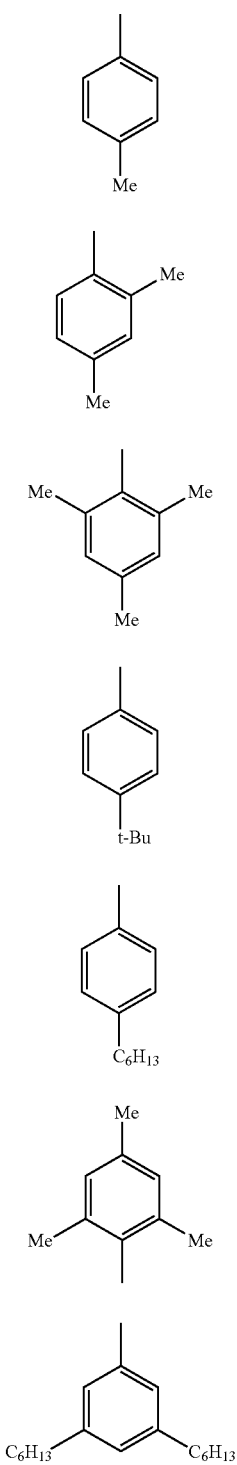
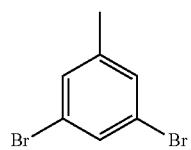
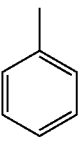
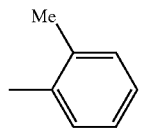
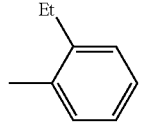
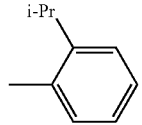
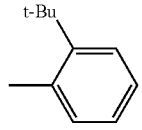
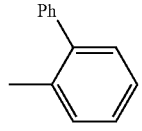
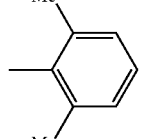
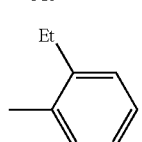

$R^2$ and $R^3$ represent preferably a hydrogen atom, an alkyl group, a cycloalkyl group or an aryl group, more preferably a hydrogen atom or an alkyl group, and the foregoing groups optionally have a substituent. $R^2$ and $R^3$ represent further preferably a hydrogen atom or an alkyl group having no substituent.

It may be permissible that one of $R^2$ and $R^3$ is a hydrogen atom and the other is an alkyl group, a cycloalkyl group or an aryl group. Further, both $R^2$ and $R^3$ may be a hydrogen atom, and both the groups may also be an alkyl group, a cycloalkyl group or an aryl group.

Suitable examples of $R^2$ and $R^j$ include groups represented by the formulae (II-01) to (II-14).

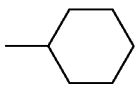

For Ring A, the ring carrying $R^2$ and $R^3$ is preferably a 6-membered aromatic hydrocarbon ring or a 6-membered aromatic heterocyclic ring, more preferably a 6-membered aromatic hydrocarbon ring, and the foregoing rings optionally have a substituent.

Ring A is preferably a monocyclic aromatic hydrocarbon ring, an aromatic hydrocarbon ring having a condensed ring, a monocyclic aromatic heterocyclic ring or an aromatic heterocyclic ring having a condensed ring, more preferably a monocyclic aromatic hydrocarbon ring, an aromatic hydrocarbon ring having a condensed ring or an aromatic heterocyclic ring having a condensed ring, further preferably a monocyclic aromatic hydrocarbon ring or an aromatic hydrocarbon ring having a condensed ring, particularly preferably a monocyclic aromatic hydrocarbon ring, and the foregoing rings optionally have a substituent.

The aromatic hydrocarbon ring represented by Ring A is preferably a benzene ring, a naphthalene ring, a fluorene ring, an indene ring or a phenanthrene ring, more preferably a benzene ring, a fluorene ring or a phenanthrene ring, further preferably a benzene ring, and the foregoing rings optionally have a substituent.

The aromatic heterocyclic ring represented by Ring A is preferably a dibenzofuran ring, a dibenzothiophene ring, a carbazole ring, a pyridine ring, a diazabenzene ring or a triazine ring, more preferably a dibenzofuran ring, a dibenzothiophene ring or a carbazole ring, and the foregoing rings optionally have a substituent.

The substituent other than $R^2$ and $R^3$ which Ring A optionally has is preferably an alkyl group, a cycloalkyl group, an aryl group or a monovalent heterocyclic group, more preferably an alkyl group, a cycloalkyl group or an aryl group, further preferably an alkyl group or an aryl group, and the foregoing rings further optionally have a substituent.

Ring A includes, for example, structures represented by the formulae (L-1) to (L-16). Of them, Ring A includes preferably structures represented by the formulae (L-1) to (L-10), more preferably structures represented by the formulae (L-1) to (L-6), particularly preferably structures represented by the formula (L-1) or (L-2). The connecting bond indicates a bond to an adjacent nitrogen atom.

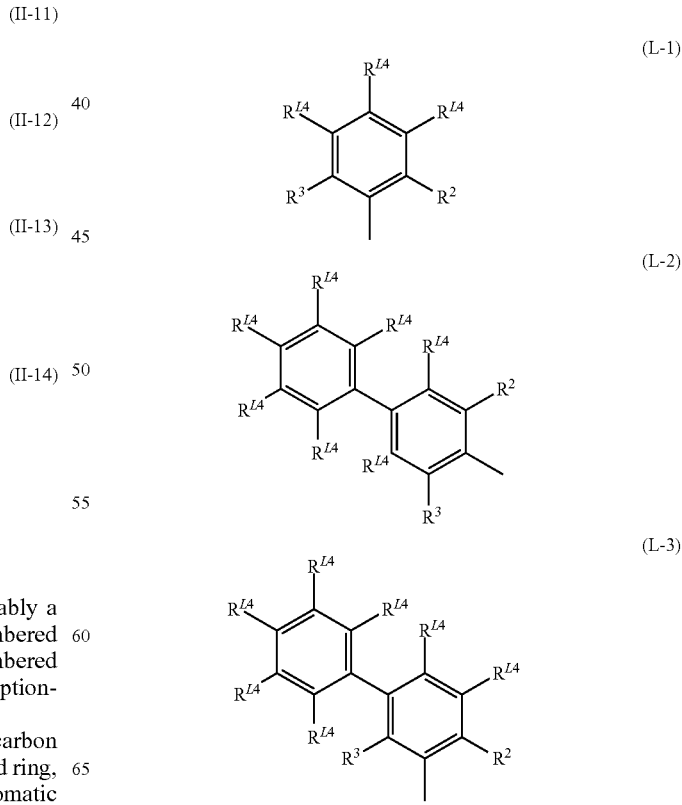

-continued
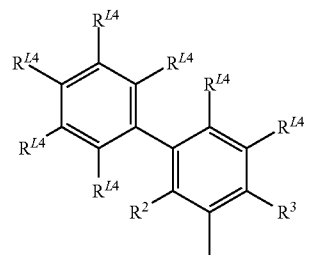
(L-4)
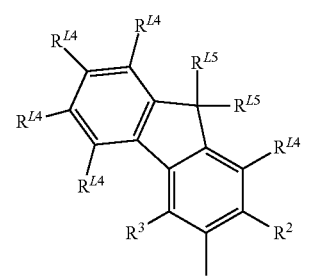
(L-5)
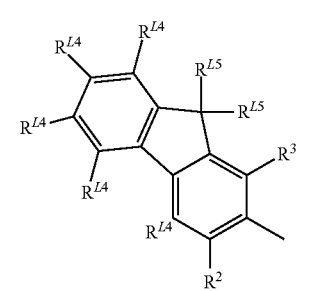
(L-6)
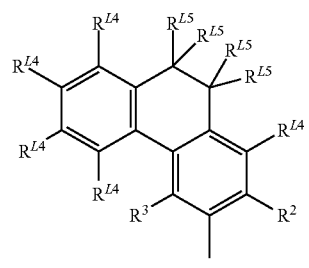
(L-7)
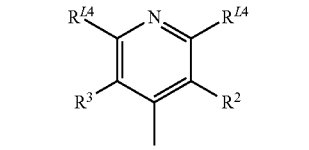
(L-8)
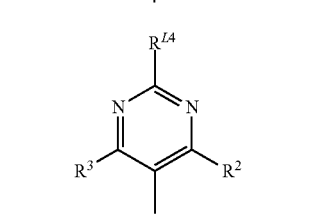
(L-9)
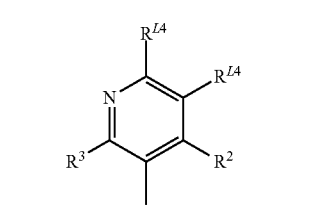
(L-10)
-continued
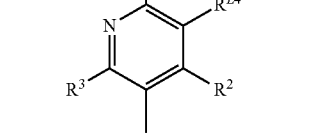
(L-11)
(L-12)
(L-13)
(L-14)
(L-15)

-continued (L-16)
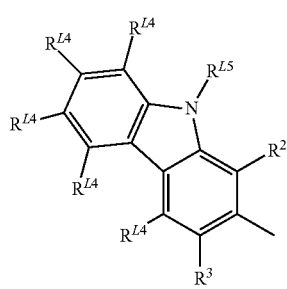

In the formulae,

R² and R³ represent the same meaning as described above.

$R^{L4}$ represents a hydrogen atom, an alkyl group, a cycloalkyl group, an aryl group or a monovalent heterocyclic group, and the foregoing groups optionally have a substituent. A plurality of $R^{L4}$ may be the same or different, and adjacent $R^{L4}$ may be combined together to form a ring together with the carbon atoms to which they are attached.

$R^{L5}$ represents an alkyl group, a cycloalkyl group, an aryl group or a monovalent heterocyclic group, and the foregoing groups optionally have a substituent. A plurality of $R^{L5}$ may be the same or different, and may be combined together to form a ring together with the carbon atoms to which they are attached.

$R^{L4}$ is preferably a hydrogen atom, an alkyl group or a cycloalkyl group, more preferably a hydrogen atom or an alkyl group, and the foregoing groups optionally have a substituent.

As the alkyl group or the cycloalkyl group represented by $R^{L4}$, groups represented by the formulae (III-01) to (III-10) are preferable.

—Me (III-01)

—Et (III-02)

—C₃H₇ (III-03)

—i-C₃H₇ (III-04)

—Bu (III-05)

—t-Bu (III-06)

—C₆H₁₃ (III-07)

—C₈H₁₇ (III-08)

(III-09)

(III-10)

$R^{L5}$ is preferably an alkyl group, a cycloalkyl group or an aryl group, more preferably an aryl group, and the foregoing groups optionally have a substituent. As the aryl group represented by $R^{L5}$, groups represented by the formulae (IV-01) to (IV-09) are preferable.

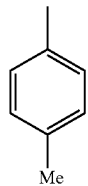
(IV-01)

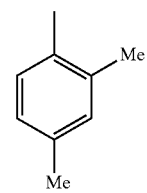
(IV-02)

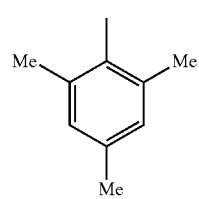
(IV-03)

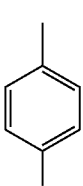
(IV-04)

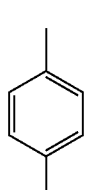
(IV-05)

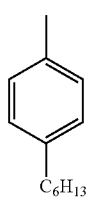
(IV-06)

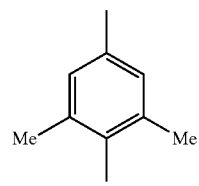
(IV-07)

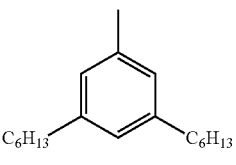
(IV-08)

(IV-09)

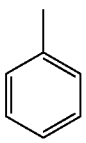

Ring B is preferably a 6-membered aromatic hydrocarbon ring or a 6-membered aromatic heterocyclic ring, more preferably a 6-membered aromatic hydrocarbon ring, and the foregoing rings optionally have a substituent.

Ring B is preferably a monocyclic aromatic hydrocarbon ring, an aromatic hydrocarbon ring having a condensed ring, a monocyclic aromatic heterocyclic ring, or an aromatic heterocyclic ring having a condensed ring, more preferably a monocyclic aromatic hydrocarbon ring, an aromatic hydrocarbon ring having a condensed ring, or an aromatic heterocyclic ring having a condensed ring, further preferably a monocyclic aromatic hydrocarbon ring, or an aromatic hydrocarbon ring having a condensed ring, particularly preferably a monocyclic aromatic hydrocarbon ring, and the foregoing rings optionally have a substituent.

Ring B includes, for example, a benzene ring, a naphthalene ring, a fluorene ring, an indene ring, a phenanthrene ring, a dibenzofuran ring, a dibenzothiophene ring, a carbazole ring, a pyridine ring, a diazabenzene ring and a triazine ring. Ring B is preferably a benzene ring, a fluorene ring, an indene ring, a phenanthrene ring, a dibenzofuran ring, a dibenzothiophene ring, a carbazole ring, a pyridine ring, a diazabenzene ring or a triazine ring, more preferably a benzene ring, a fluorene ring, a phenanthrene ring, a dibenzofuran ring, a dibenzothiophene ring, a carbazole ring, a pyridine ring, a diazabenzene ring or a triazine ring, further preferably a benzene ring, a fluorene ring, a dibenzofuran ring, a dibenzothiophene ring, a carbazole ring, a pyridine ring or a pyrimidine ring, particularly preferably a benzene ring, a fluorene ring, a dibenzofuran ring or a dibenzothiophene ring, especially preferably a benzene ring, and the foregoing rings optionally have a substituent.

The substituent which Ring B optionally has is preferably an alkyl group, a cycloalkyl group, an aryl group, a monovalent heterocyclic group or a halogen atom, more preferably an alkyl group, a cycloalkyl group or an aryl group, further preferably an alkyl group or an aryl group, and the foregoing groups further optionally have a substituent.

In the production method according to the present embodiment, the amide compound represented by the formula (2) may be a compound represented by the formula (2a).

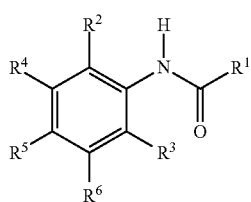

(2a)

$R^4$, $R^5$ and $R^6$ represent preferably a hydrogen atom, an alkyl group, a cycloalkyl group, an aryl group or a monovalent heterocyclic group, more preferably a hydrogen atom, an alkyl group or an aryl group, and the foregoing groups optionally have a substituent.

Suitable examples of $R^4$, $R^5$ and $R^6$ include groups represented by the formulae (II-01) to (II-17), a group represented by the formula (D-A), and a group represented by the formula (D-B).

—Me (II-01)

—Et (II-02)

—$C_3H_7$ (II-03)

—i-$C_3H_7$ (II-04)

—Bu (II-05)

—t-Bu (II-06)

—$C_6H_{13}$ (II-07)

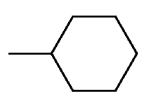 (II-08)

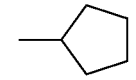 (II-09)

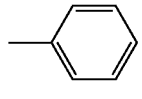 (II-10)

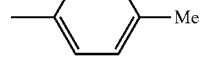 —Me (II-11)

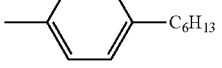 —$C_6H_{13}$ (II-12)

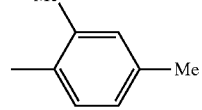 (II-13)

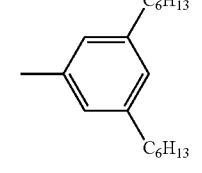 (II-14)

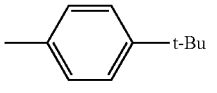 —t-Bu (II-15)

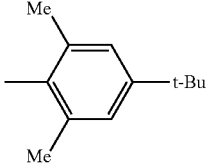 —t-Bu (II-16)

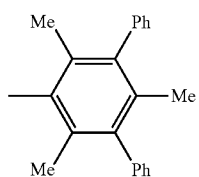
(II-17)
For $R^4$, $R^5$ and $R^6$, suitable examples of the group represented by the formula (D-A) or (D-B) include, for example, groups represented by the formulae (II-18) to (II-23).
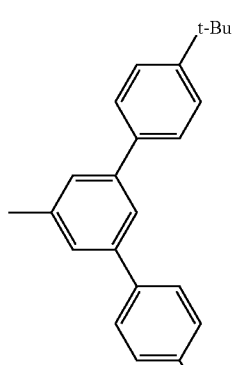
(II-18)
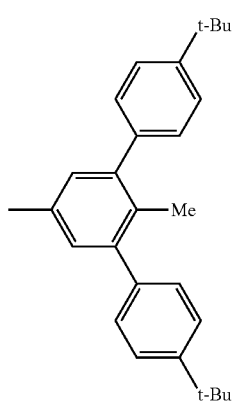
(II-19)
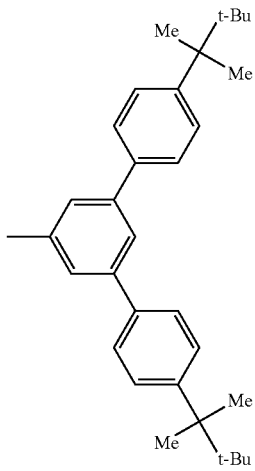
(II-20)
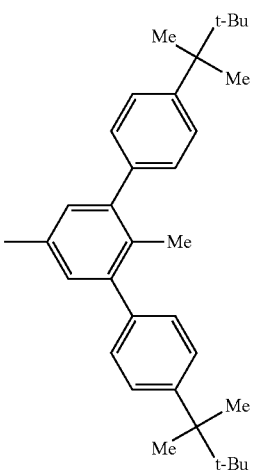
(II-21)
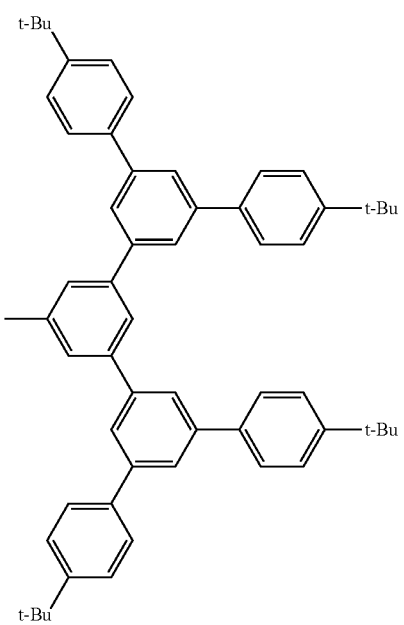
(II-22)

-continued (II-23)

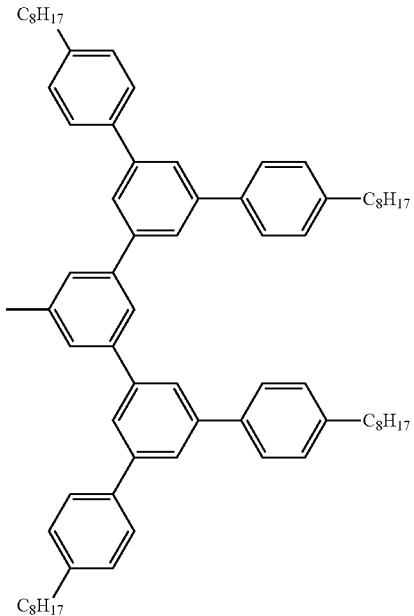

In the production method according to the present embodiment, the hydrazide compound represented by the formula (3) may be a salt such as a hydrochloride.

In the production method according to the present embodiment, the hydrazide compound represented by the formula (3) may be a compound represented by the formula (3a).

(3a)

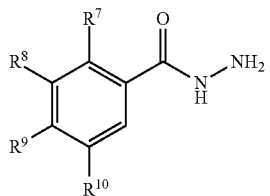

$R^7$ and $R^{10}$ represent preferably a hydrogen atom, an alkyl group, a cycloalkyl group, an aryl group, a monovalent heterocyclic group or a halogen atom, more preferably a hydrogen atom, an alkyl group or an aryl group, further preferably a hydrogen atom, and the foregoing groups optionally have a substituent.

$R^8$ and $R^9$ represent preferably a hydrogen atom, an alkyl group, a cycloalkyl group, an aryl group, a monovalent heterocyclic group or a halogen atom, more preferably a hydrogen atom, an alkyl group, a cycloalkyl group or an aryl group, further preferably a hydrogen atom, an alkyl group or an aryl group, and the foregoing groups optionally have a substituent.

Suitable examples of $R^8$ and $R^9$ include groups represented by the formulae (II-01) to (II-17), a group represented by the formula (D-A), and a group represented by the formula (D-B).

For $R^8$ and $R^9$, suitable examples of the group represented by the formula (D-A) or (D-B) include groups represented by the formulae (II-18) to (II-23).

The 1,2,4-triazole compound obtained by the production method according to the present embodiment may be, for example, a compound represented by the formula (1a).

(1a)

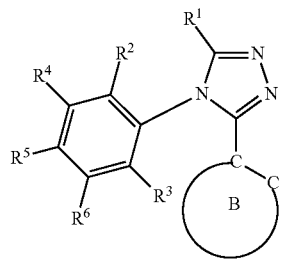

Further, the 1,2,4-triazole compound obtained by the production method according to the present embodiment may be, for example, a compound represented by the formula (1b).

(1b)

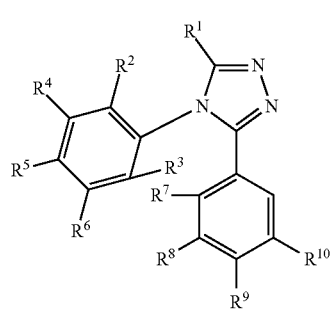

Examples of the 1,2,4-triazole compound obtained by the production method according to the present embodiment include compounds represented by the following formulae (Tr-01) to (Tr-07).

(Tr-01)

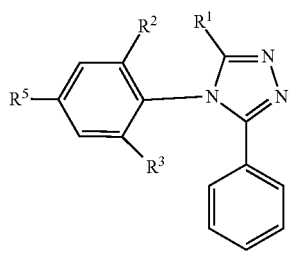

(Tr-02)

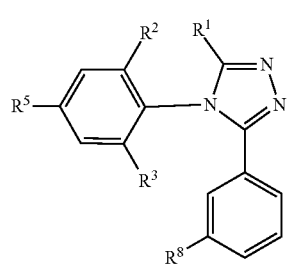

-continued
(Tr-03)
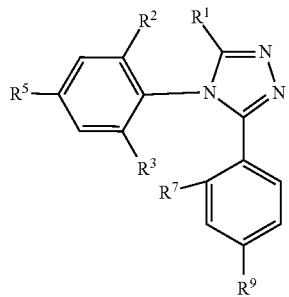
(Tr-04)
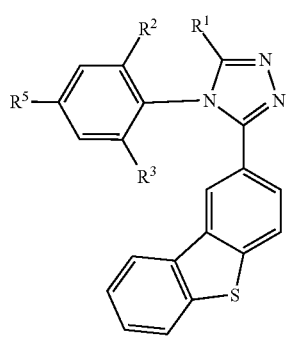
(Tr-05)
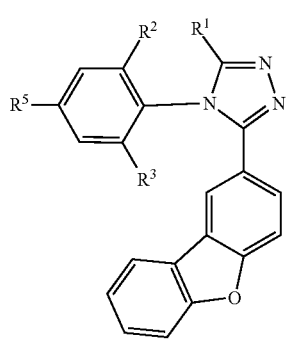
(Tr-06)
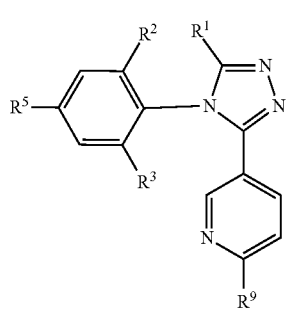
(Tr-07)
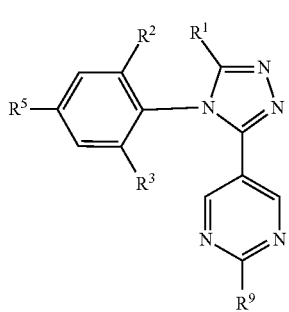
In the formulae, $R^1$, $R^2$, $R^3$, $R^5$, $R^7$, $R^8$ and $R^9$ represent the same meaning as described above.
The 1,2,4-triazole compound obtained by the production method according to the present embodiment includes, for example, compounds represented by the following formulae.
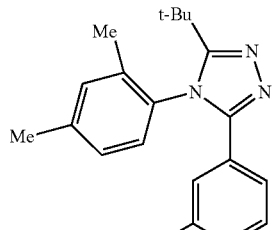
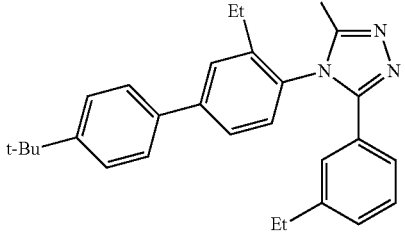
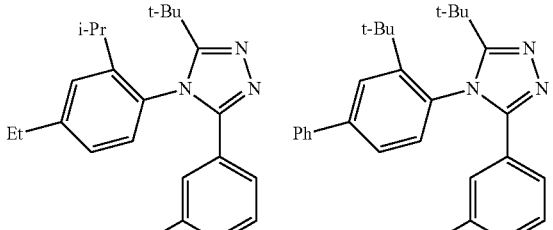
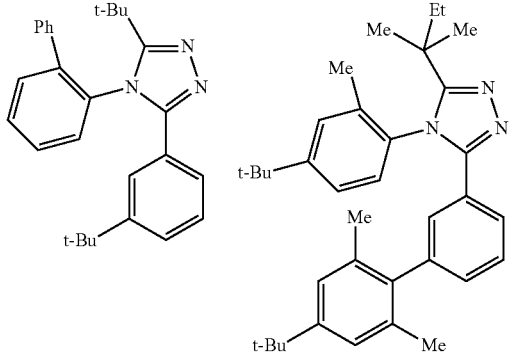
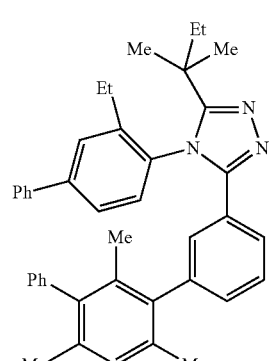

-continued
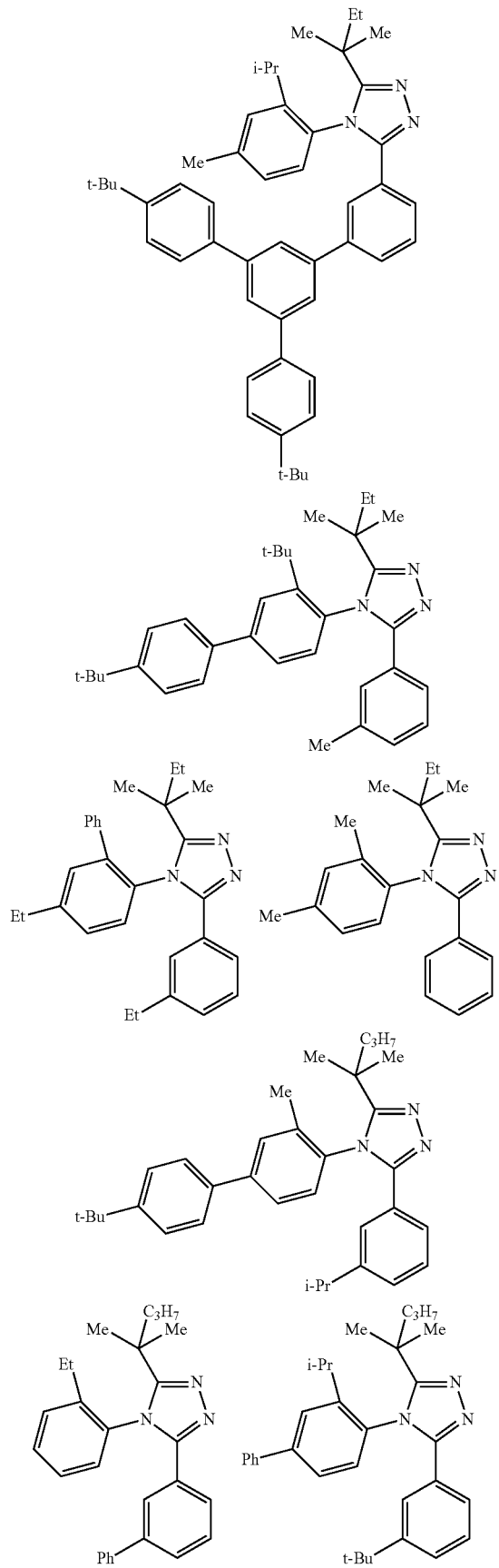
-continued
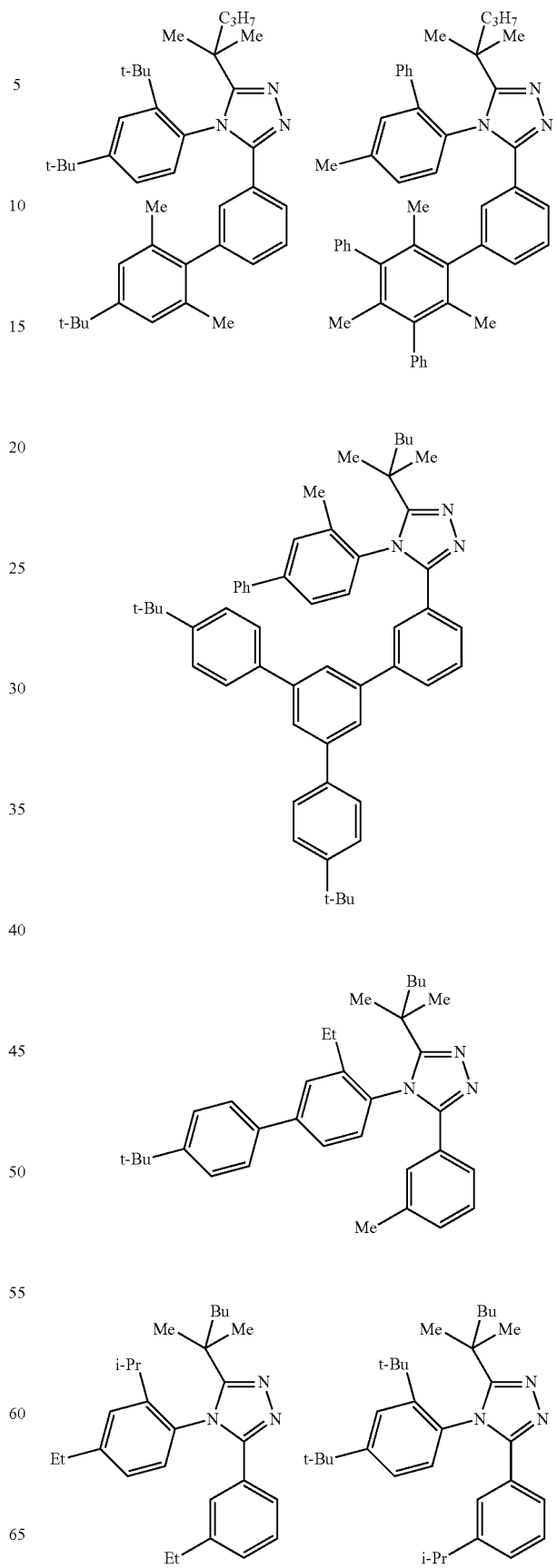

-continued
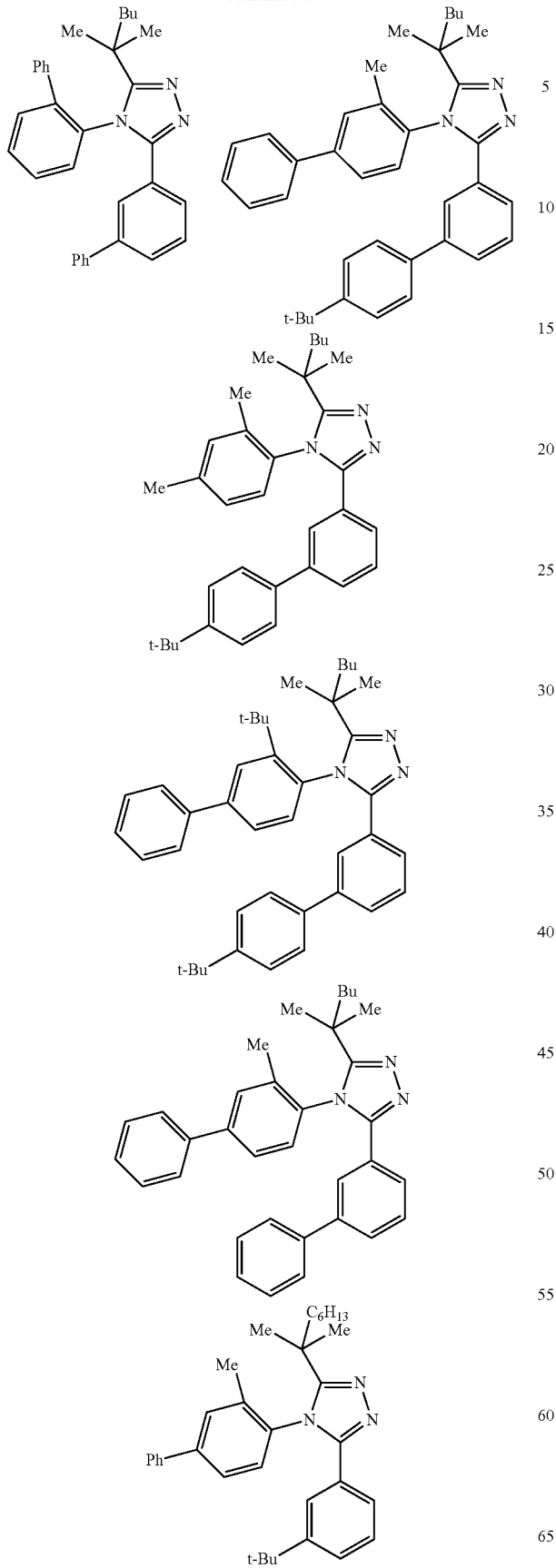
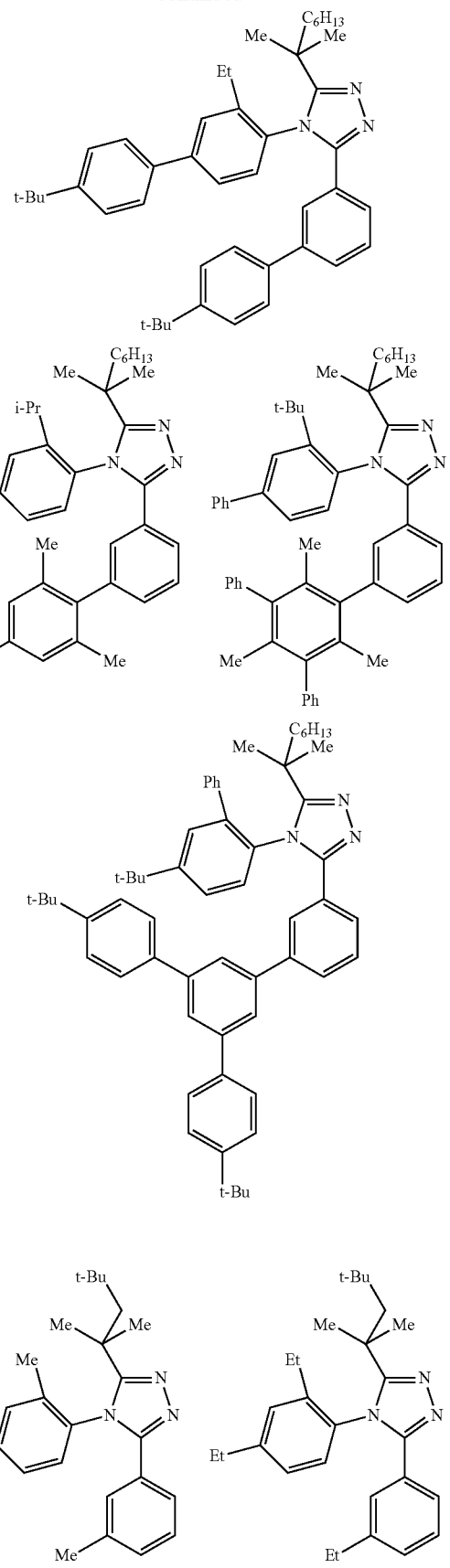

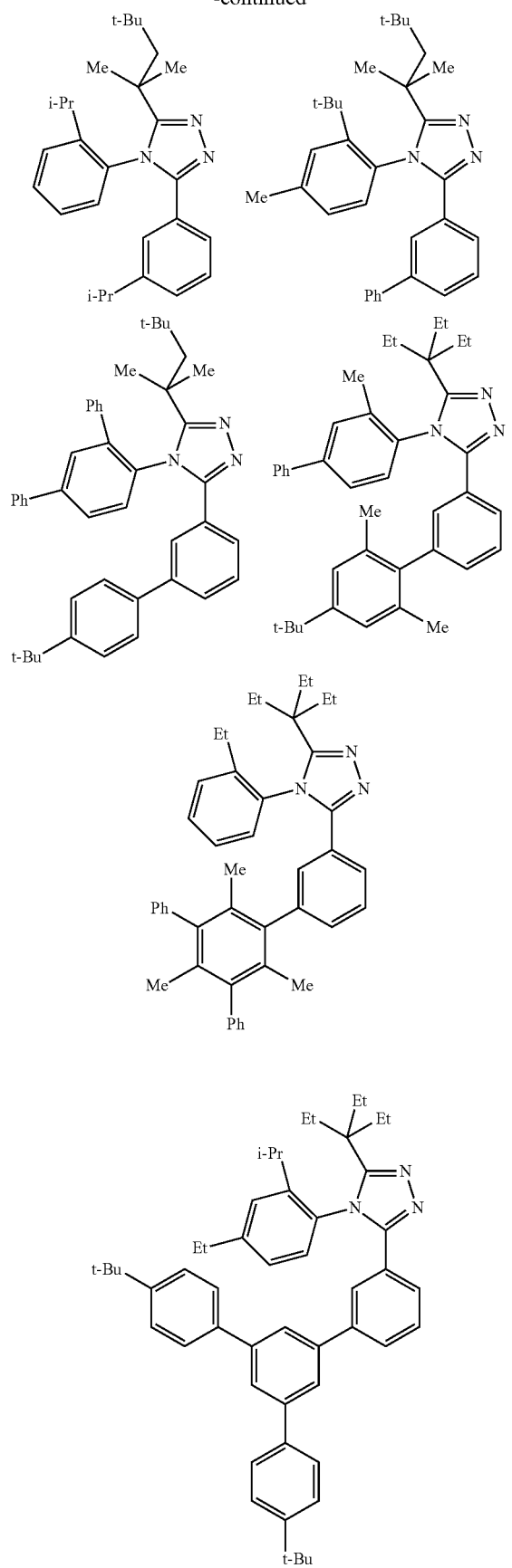
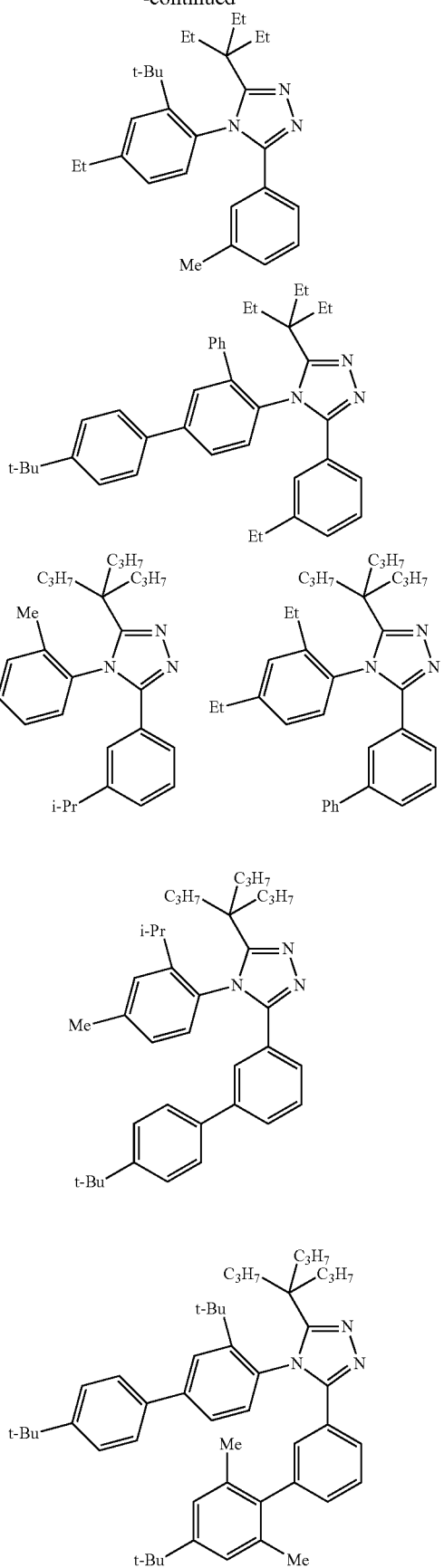

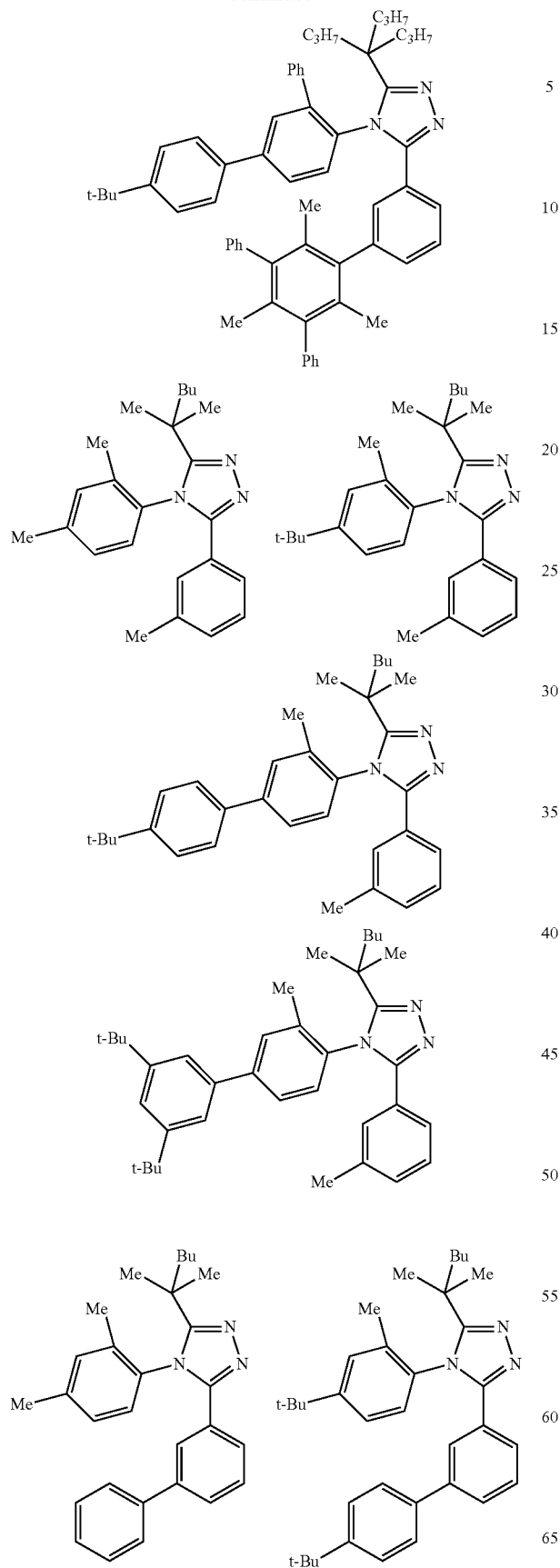
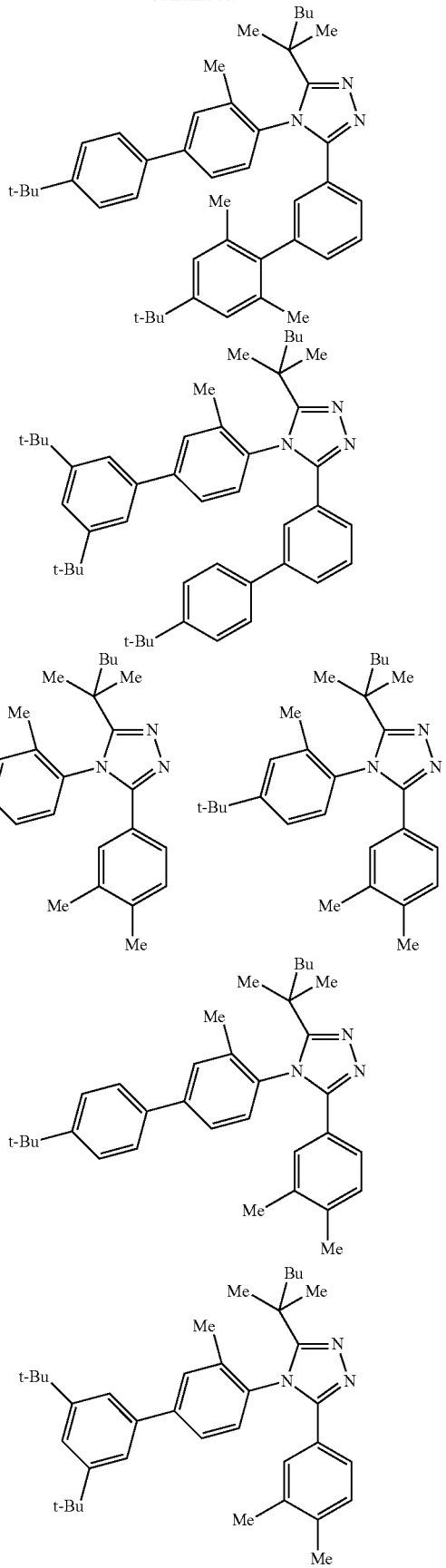

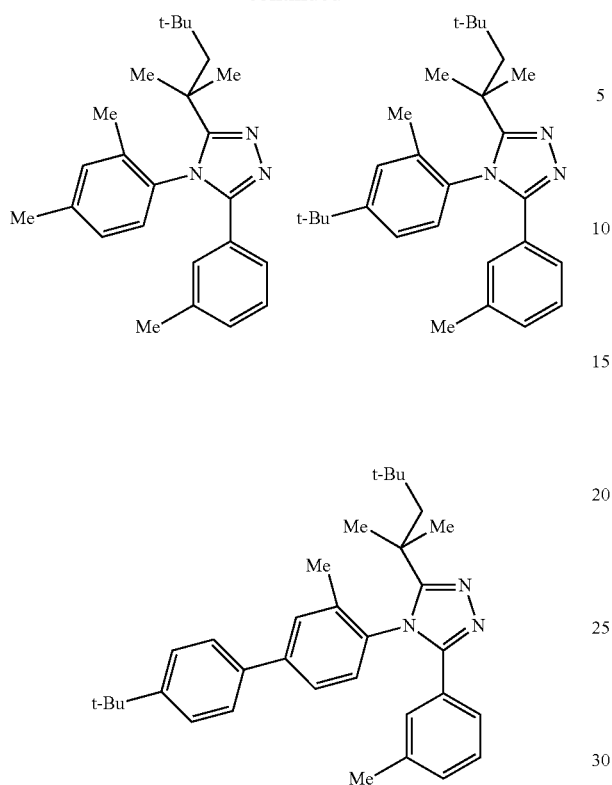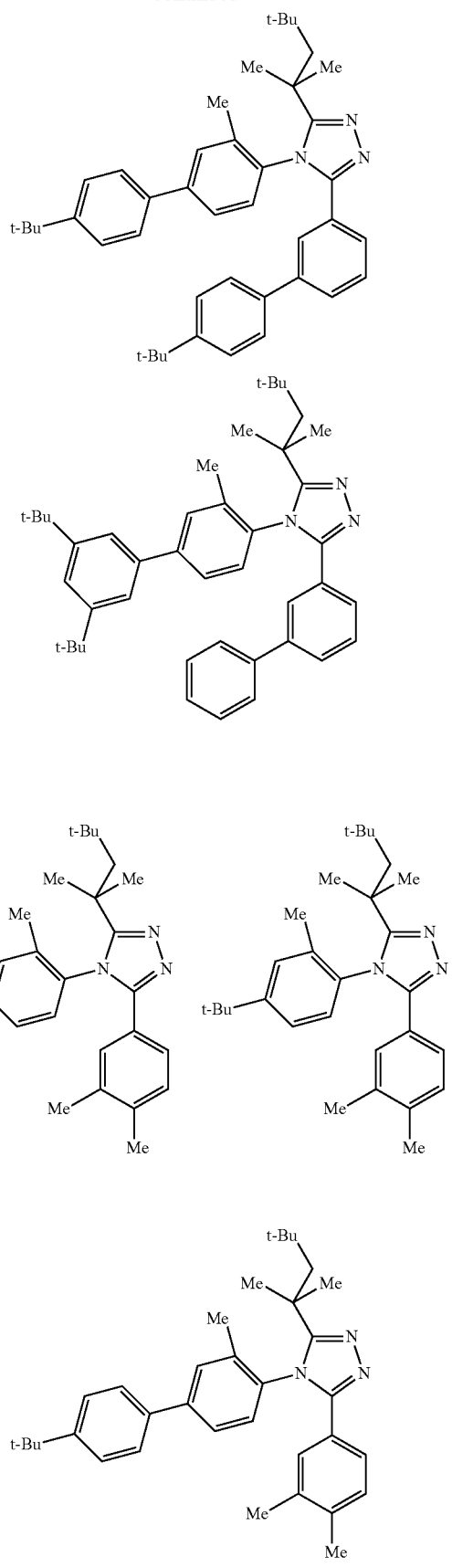

-continued
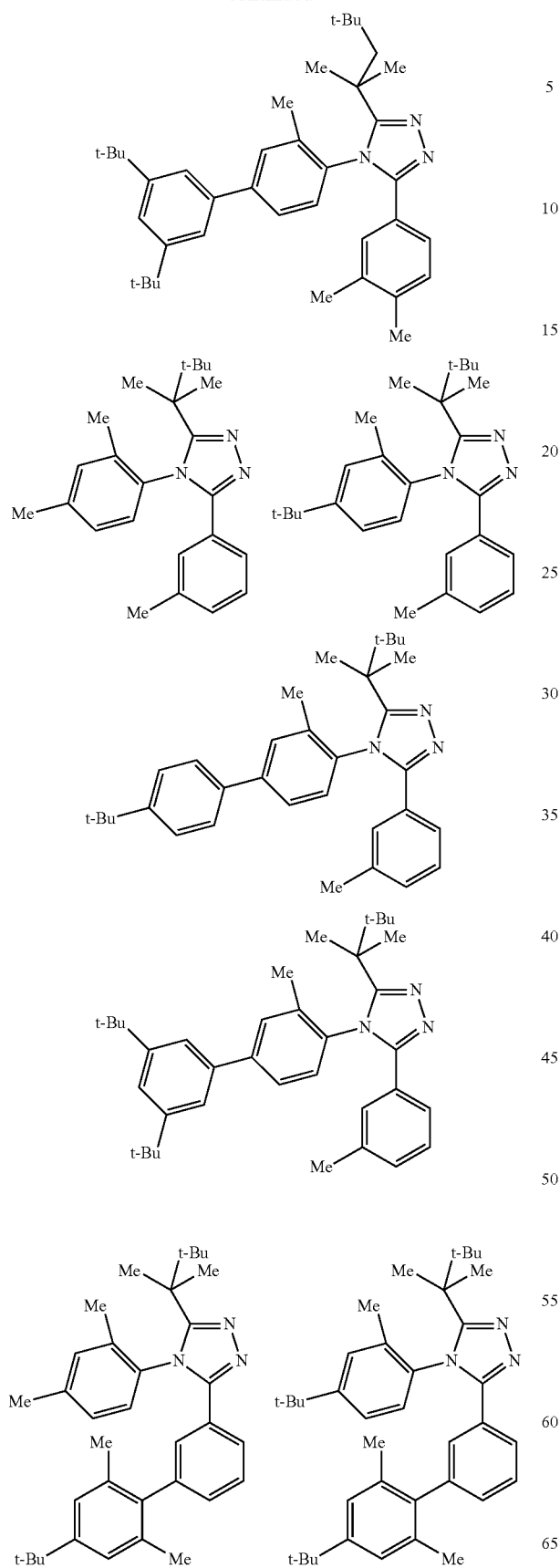
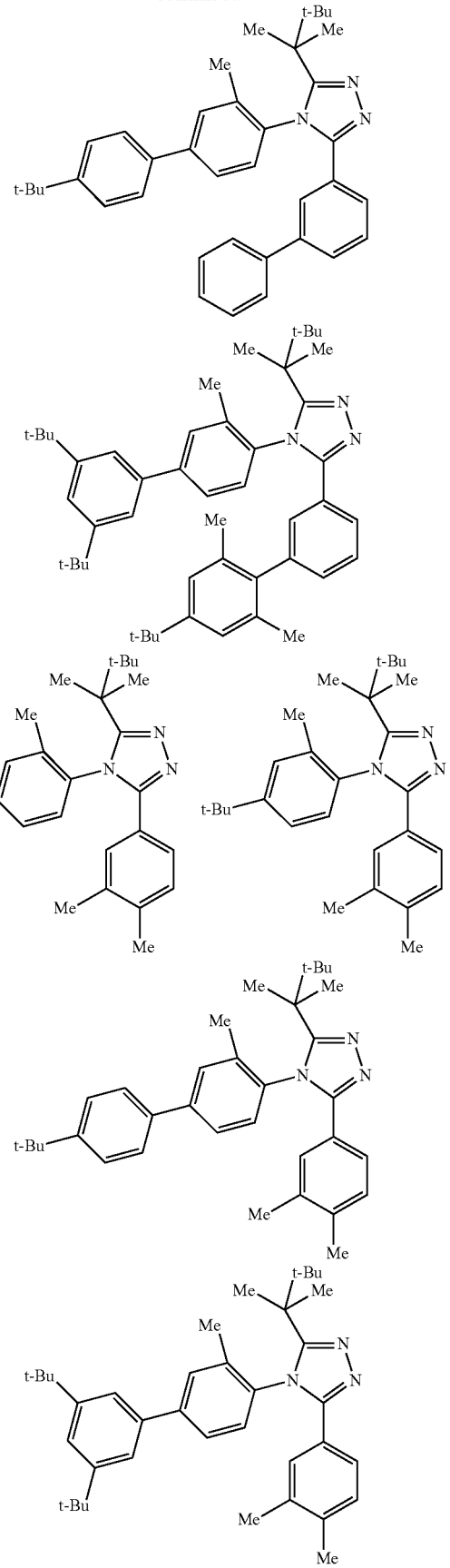

53
-continued
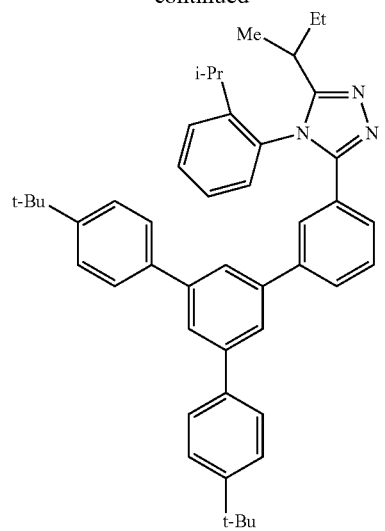
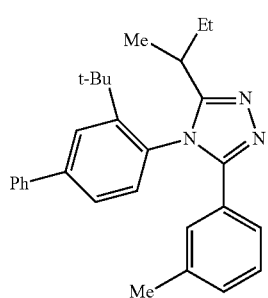
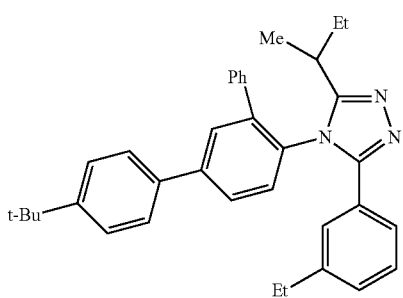
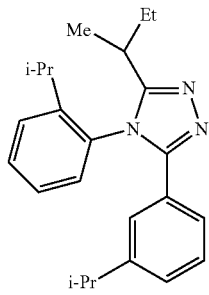 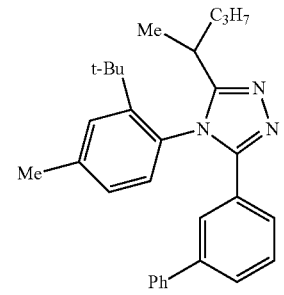
54
-continued
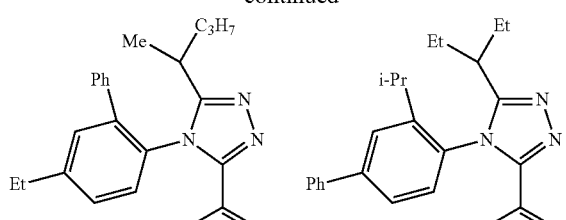
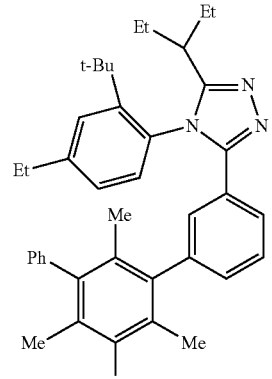
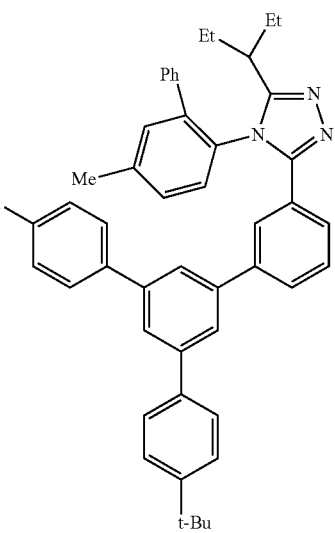
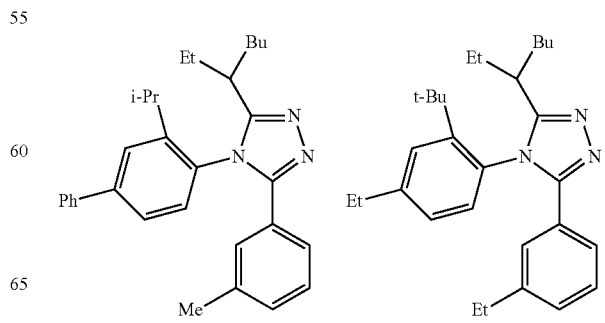

55
-continued
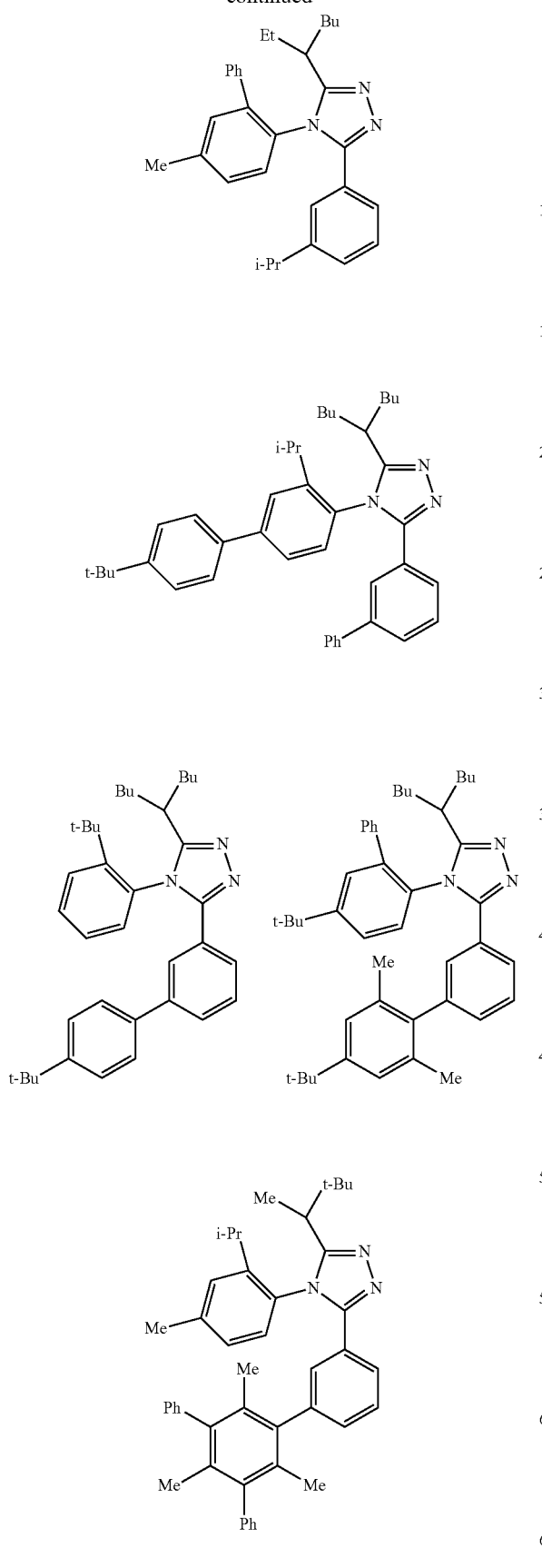
56
-continued
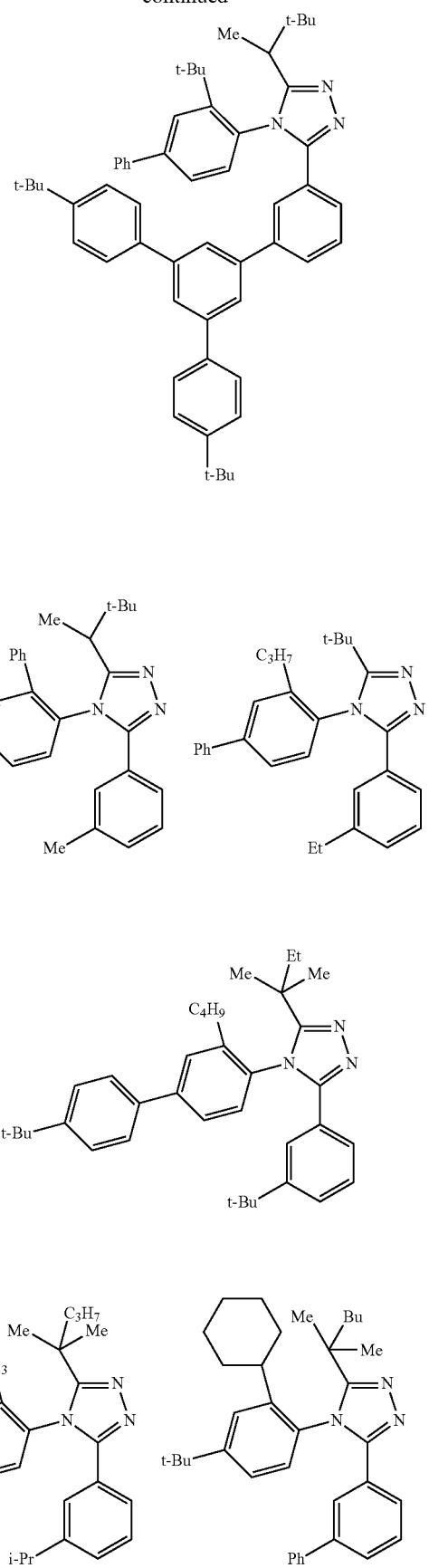

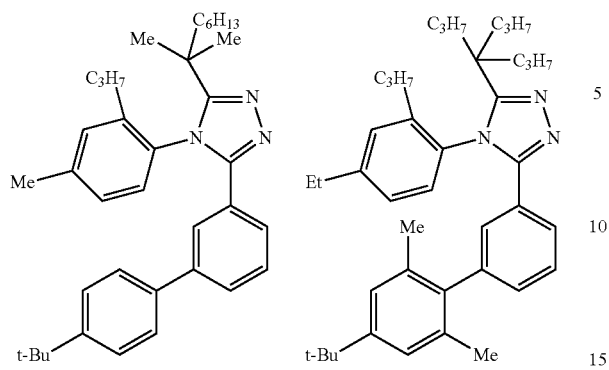
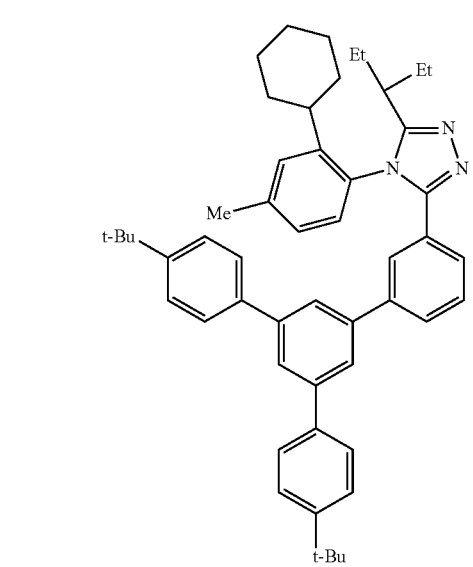
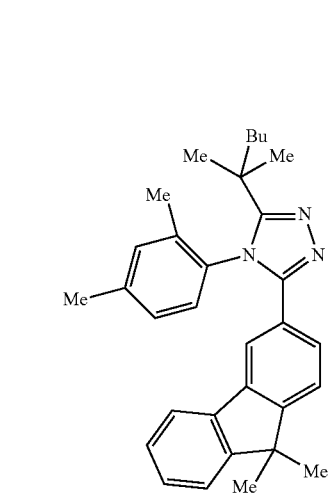
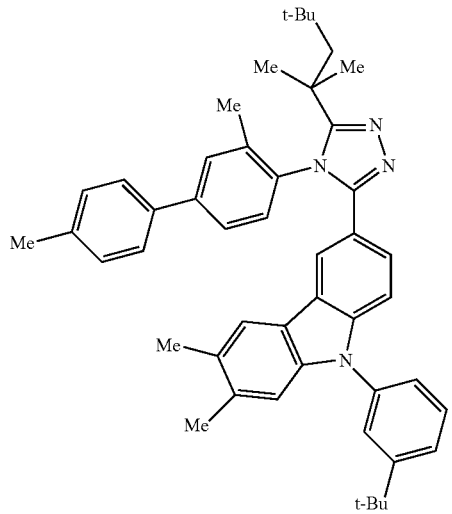
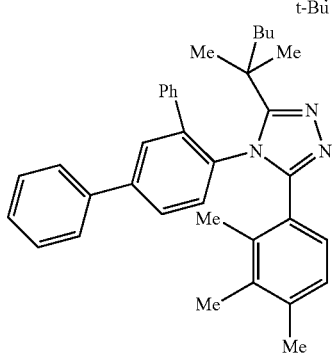
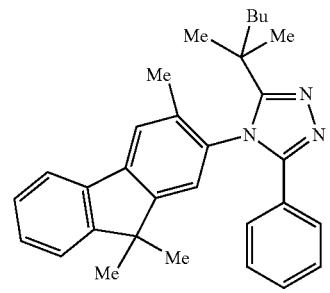
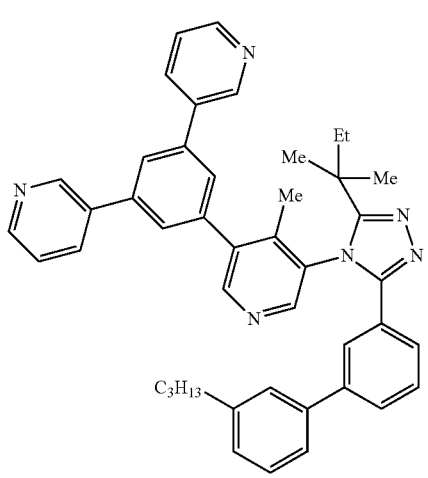

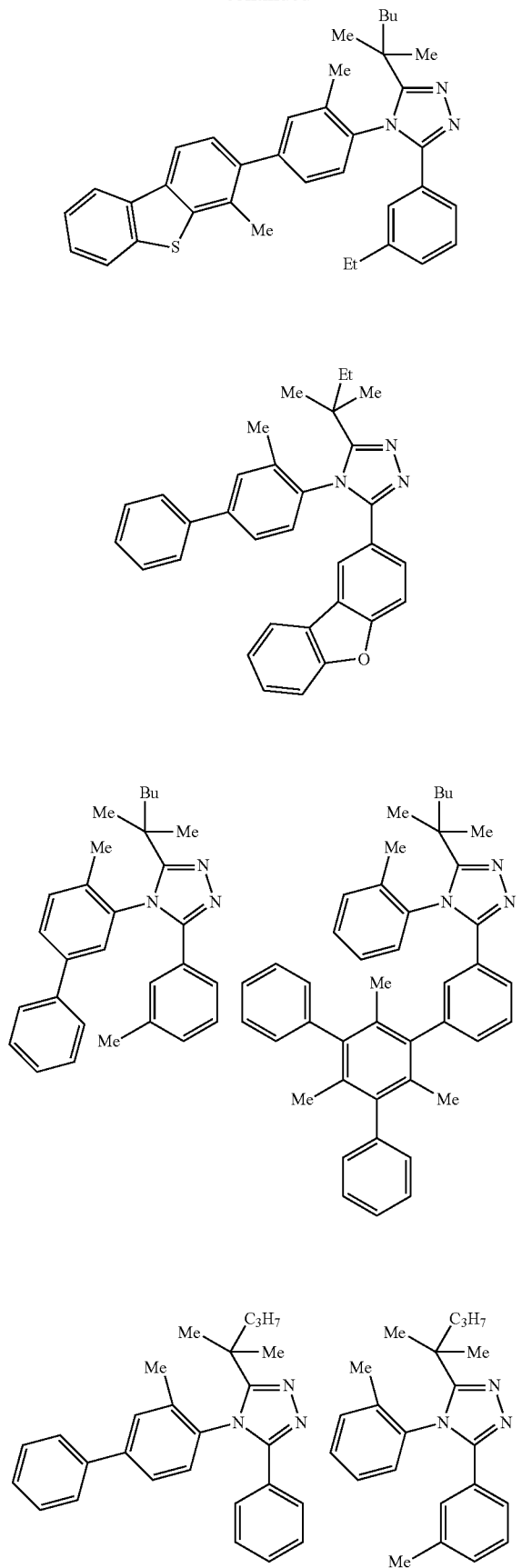
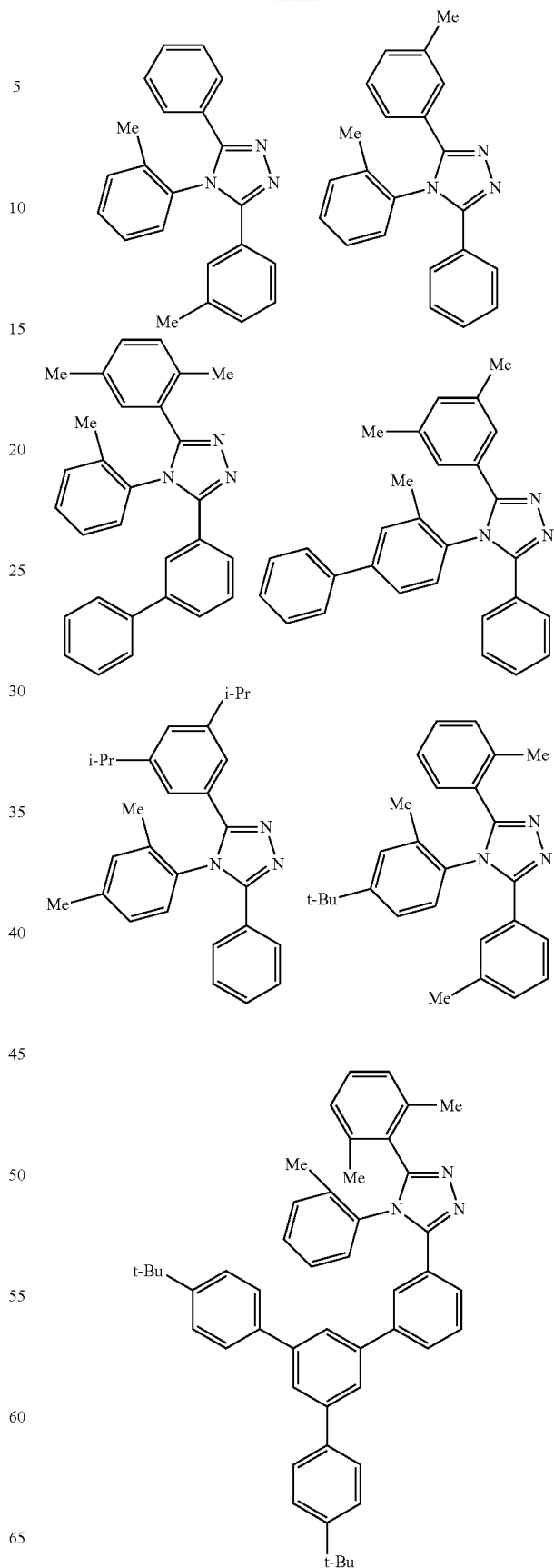

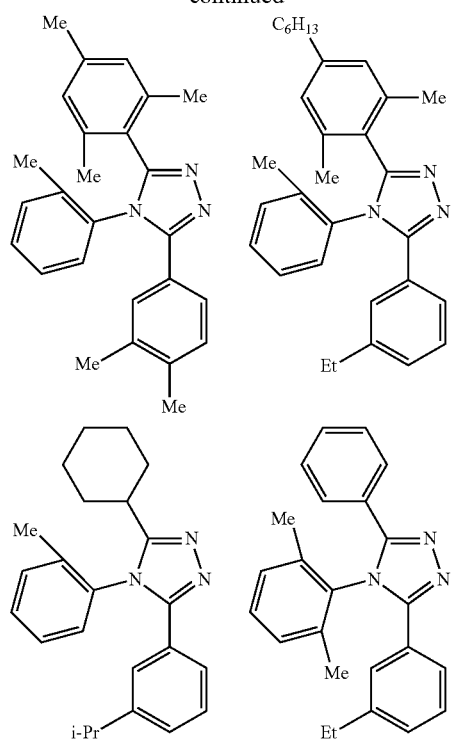
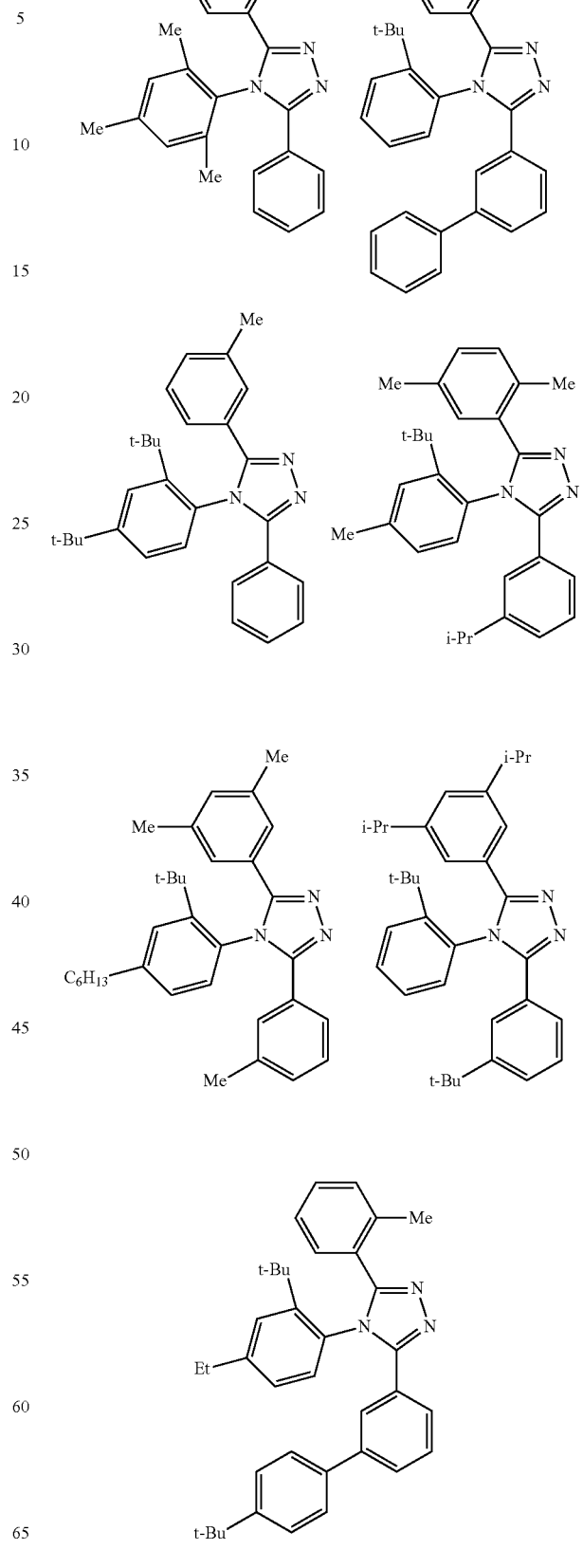

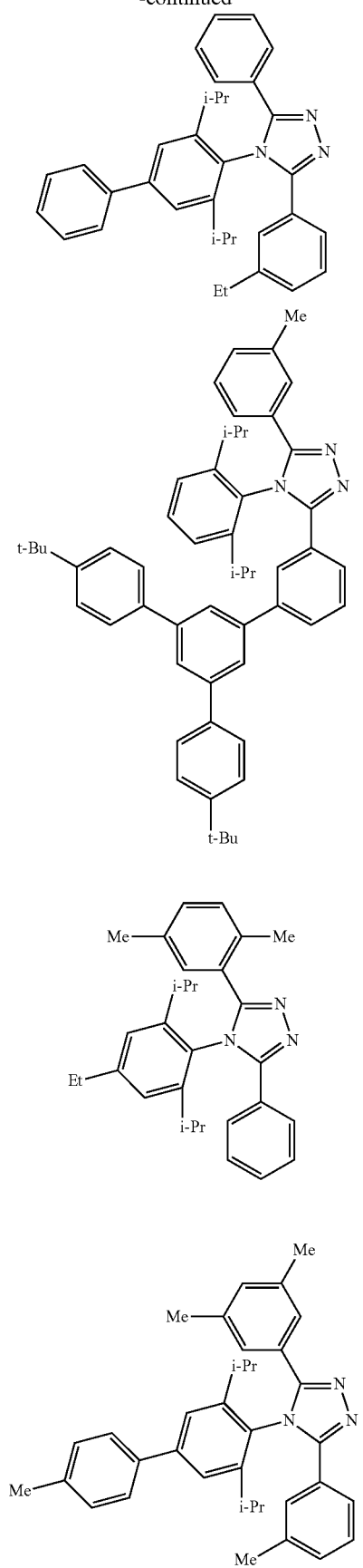
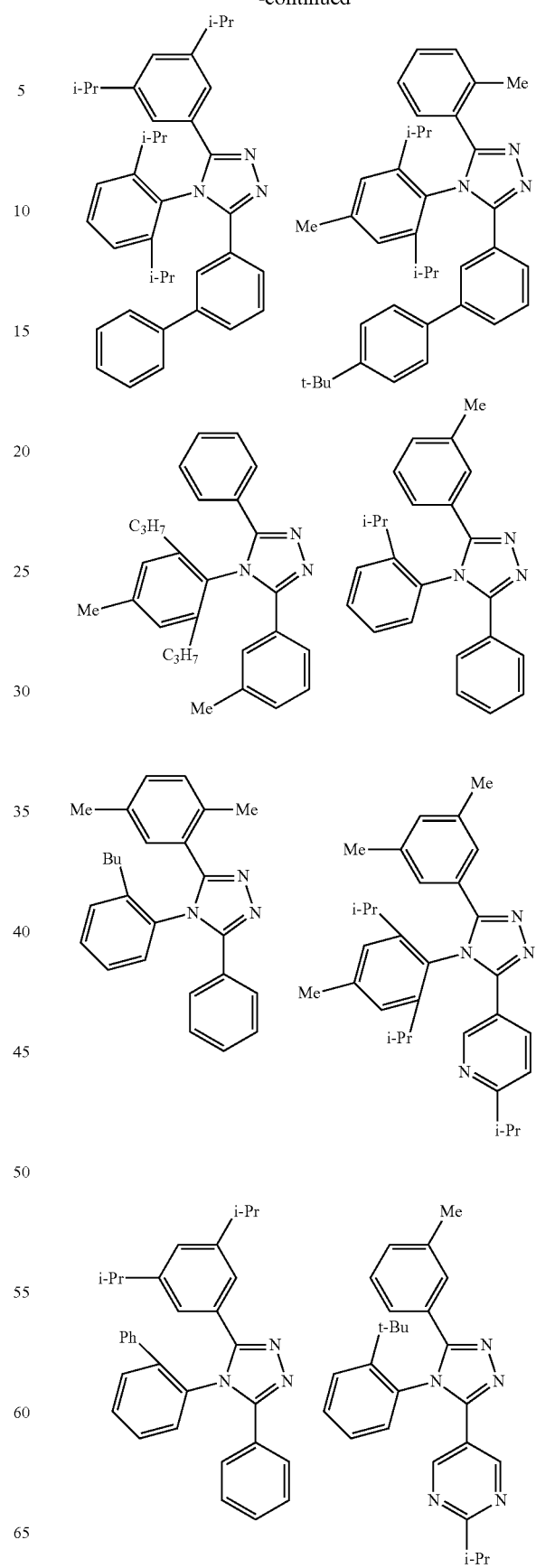

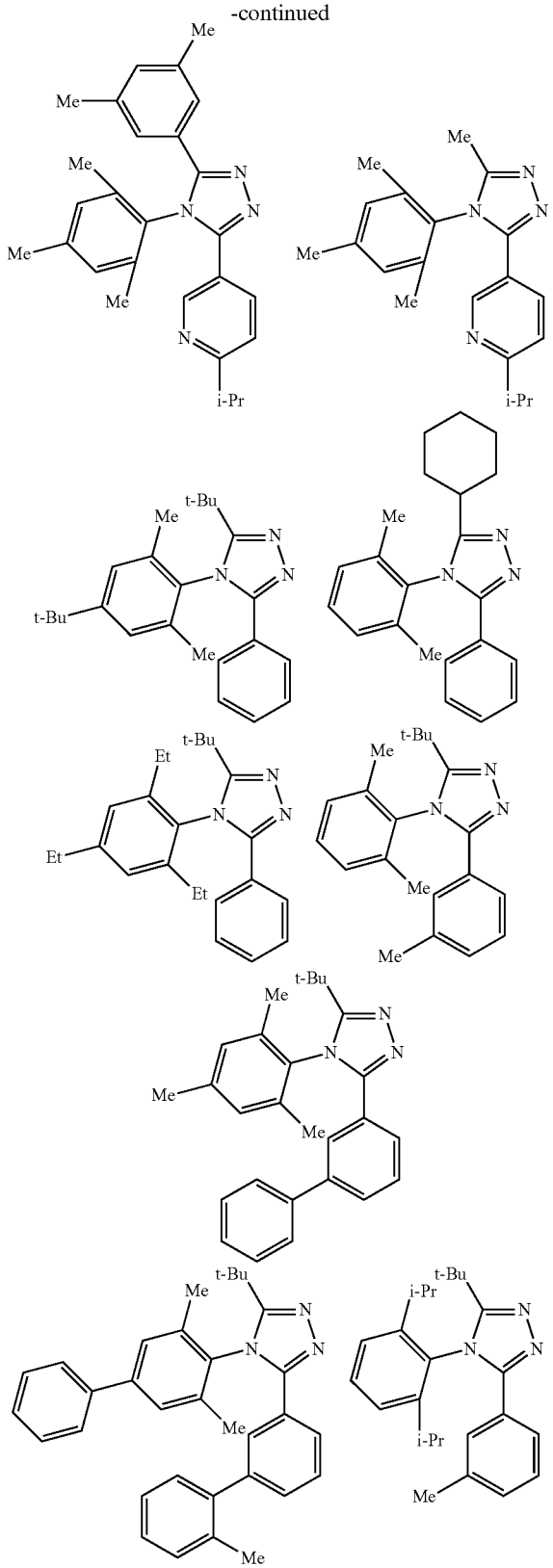

Examples of the 1,2,4-triazole compound described above can be those in which suitable embodiments of Ring A, Ring B, $R^1$, $R^2$, $R^3$, $R^4$, $R^5$, $R^6$, $R^7$, $R^8$, $R^9$ and $R^{10}$ are shown, and suitable examples of Ring A, Ring B, $R^1$, $R^2$, $R^3$, $R^4$, $R^5$, $R^6$, $R^7$, $R^8$, $R^9$ and $R^{10}$ include respective groups in examples of the 1,2,4-triazole compound described above.

Further, compounds in which Ring A, Ring B, $R^1$, $R^2$, $R^3$, $R^4$, $R^5$, $R^6$, $R^7$, $R^8$, $R^9$ and $R^{10}$ as exemplified in the 1,2,4-triazole compound described above are optionally combined can also be exemplified as suitable 1,2,4-triazole compounds.

In the production method according to the present embodiment, the reaction of an amide compound represented by the formula (2) with a hydrazide compound represented by the formula (3) is performed in a solvent in the presence of a Lewis acid and a Lewis base.

The Lewis acid includes, for example, metal or semimetal compounds such as iron(III) chloride, aluminum(III) chloride, zinc (II) chloride, titanium (IV) chloride, copper (II) chloride, palladium(II) chloride, trimethylsilyl chloride, triphenylsilyl chloride, boron trifluoride•diethyl ether complex, zinc(II) trifluoromethanesulfonate, aluminum(III) trifluoromethanesulfonate, trimethylsilyl triflate and acetylacetonezinc(II); acid halides such as carboxylic halides, sulfonic halides and phosphoric halides; ester compounds such as carboxylates, sulfonates and phosphates; and, acid anhydrides such as carboxylic anhydrides, sulfonic anhydrides and phosphoric anhydrides. The Lewis acid is preferably an acid halide, an ester compound or an acid anhydride, more preferably an acid anhydride.

In the acid halide, the ester compound and the acid anhydride, the acid is preferably a carboxylic acid, a sulfonic acid or phosphoric acid, more preferably a carboxylic acid or a sulfonic acid, further preferably a sulfonic acid, because the yield of the 1,2,4-triazole compound is improved.

When the acid halide, the ester compound and the acid anhydride are a carboxylic halide, a carboxylic acid ester compound and a carboxylic anhydride respectively, the carboxylic acid includes, for example, aliphatic carboxylic acids such as acetic acid, trifluoroacetic acid and propionic acid, and, aromatic carboxylic acids such as benzoic acid and aliphatic carboxylic acids are preferable, acetic acid or trifluoroacetic acid is more preferable.

When the acid halide, the ester compound and the acid anhydride are a sulfonic halide, a sulfonic acid ester compound and a sulfonic anhydride respectively, the sulfonic acid includes, for example, aliphatic sulfonic acids such as trifluoromethanesulfonic acid and methanesulfonic acid, and, aromatic sulfonic acids such as p-toluenesulfonic acid and aliphatic sulfonic acids are preferable, trifluoromethanesulfonic acid is more preferable.

In the production method according to the present embodiment, the Lewis acid is preferably a carboxylic anhydride, a sulfonic anhydride or a phosphoric anhydride, more preferably a carboxylic anhydride or a sulfonic anhydride, further preferably a sulfonic anhydride, particularly preferably an aliphatic sulfonic anhydride, because the yield of the 1,2,4-triazole compound is more improved.

The use amount of a Lewis acid in the above-described reaction is preferably 0.01 to 30 molar equivalents, more preferably 0.1 to 20 molar equivalents, further preferably 1 to 10 molar equivalents, with respect to the total molar number of an amide compound represented by the formula (2).

The Lewis acids may be used each singly or two or more of them may be used in combination.

The Lewis base is preferably an organic base.

The organic base as the Lewis base includes, for example, aliphatic amine compounds such as triethylamine, diisopropylamine and piperidine; aromatic amine compounds such as triphenylamine; nitrogen-containing heterocyclic compounds such as pyridine and pyrimidinee; and, phosphine compounds such as triphenylphosphine, and aliphatic amine compounds, aromatic amine compounds or nitrogen-containing heterocyclic compounds are preferable, nitrogen-containing heterocyclic compounds are more preferable.

The nitrogen-containing heterocyclic compound as the Lewis base is preferably a pyridine compound, because the yield of the 1,2,4-triazole compound is improved. The pyridine compound includes, for example, pyridine; alkyl-substituted pyridine compounds such as 2,6-lutidine and 2,6-di-t-butylpyridine; and, halogen-substituted pyridine compounds such as 2-chloropyridine, 2-fluoropyridine and 2-bromopyridine, and alkyl-substituted pyridine compounds or halogen-substituted pyridine compounds are preferable, halogen-substituted pyridine compounds are more preferable, 2-chloropyridine or 2-fluoropyridine is further preferable, because the yield of the 1,2,4-triazole compound is more improved.

The use amount of a Lewis base in the above-described reaction is preferably 0.1 to 30 molar equivalents, more preferably 0.5 to 20 molar equivalents, further preferably 1 to 10 molar equivalents, with respect to the total molar number of an amide compound represented by the formula (2).

The Lewis bases may be used each singly or two or more of them may be used in combination.

The solvent is preferably selected from solvents in which an amide compound and a hydrazide compound are soluble.

The solvent includes, for example, organic solvents and water, and organic solvents are preferable.

The organic solvent includes, for example, aromatic hydrocarbon solvents such as toluene, xylene (o-xylene, m-xylene, p-xylene, and a mixture thereof), mesitylene, ethylbenzene and cyclohexylbenzene; halogenated aromatic hydrocarbon solvents such as chlorobenzene, dichlorobenzene, trichlorobenzene, bromobenzene and fluorobenzene; alcohol solvents such as methanol, ethanol, propanol, ethylene glycol, glycerin, 2-methoxyethanol and 2-ethoxyethanol; ether solvents such as tetrahydrofuran, 1,4-dioxane, dimethoxyethane, cyclopentyl methyl ether, diglyme, anisole, methylanisole and dimethoxybenzene; nitrile solvents such as acetonitrile and benzonitrile; ketone solvents such as acetone, methyl ethyl ketone, methyl isobutyl ketone, cyclohexanone and acetophenone; amide solvents such as N,N-dimethylacetamide, N,N-dimethylformamide and N-methyl-2-pyrrolidone; ester solvents such as ethyl acetate, butyl acetate and methyl benzoate; aliphatic hydrocarbon solvents such as pentane, hexane, octane, decane, cyclohexane and decaline; halogenated aliphatic hydrocarbon solvents such as chloroform, dichloromethane, dichloroethane, trichloroethylene, tetrachloroethylene, chlorobutane and bromoform; and, dimethyl sulfoxide.

The organic solvent is preferably an aromatic hydrocarbon solvent, a halogenated aromatic hydrocarbon solvent, an ether solvent, an aliphatic hydrocarbon solvent, a halogenated aliphatic hydrocarbon solvents or dimethyl sulfoxide, more preferably an aromatic hydrocarbon solvent, a halogenated aromatic hydrocarbon solvent, an aliphatic hydrocarbon solvent or a halogenated aliphatic hydrocarbon solvent, further preferably an aromatic hydrocarbon solvent or a halogenated aromatic hydrocarbon solvent, particularly preferably a halogenated aromatic hydrocarbon solvent.

In the aliphatic hydrocarbon solvent, the number of carbon atoms of an aliphatic hydrocarbon is preferably 5 to 30, more preferably 6 to 15.

In the halogenated aliphatic hydrocarbon solvent, the number of carbon atoms of a halogenated aliphatic hydrocarbon is preferably 3 to 20, more preferably 4 to 10.

The halogenated aliphatic hydrocarbon solvent is preferably a chlorinated aliphatic hydrocarbon solvent such as chloroform, dichloromethane, dichloroethane, trichloroethylene, tetrachloroethylene and chlorobutane, more preferably chlorobutane.

In the aromatic hydrocarbon solvent, the number of carbon atoms of an aromatic hydrocarbon is preferably 6 to 20, more preferably 6 to 10.

In the halogenated aromatic hydrocarbon solvent, the number of carbon atoms of a halogenated aromatic hydrocarbon is preferably 6 to 20, more preferably 6 to 10.

The halogenated aromatic hydrocarbon solvent is preferably a chlorinated aromatic hydrocarbon solvent such as chlorobenzene, dichlorobenzene and trichlorobenzene, and chlorobenzene and dichlorobenzene are more preferable.

It is preferable that the solvent is liquid at 1 atm and 25° C.

As the solvent, solvents having a boiling point of 40° C. or higher are preferable, solvents having a boiling point of 85° C. or higher are more preferable. The boiling point of the solvent may be, for example, 160° C. or lower, or may be 140° C. or lower.

In the present specification, "boiling point" denotes a boiling point at 1 atm.

The use amount of the solvent is usually 0.1 to 100 parts by mass, preferably 1 to 80 parts by mass, more preferably 5 to 50 parts by mass, when the amount of an amide compound represented by the formula (2) is 1 part by mass.

The solvents may be used each singly or two or more of them may be used in combination.

It is preferable that the temperature of the reaction of an amide compound with a hydrazide compound is a temperature not higher than the boiling point of the solvent.

The reaction temperature is preferably 30° C. or higher, more preferably 40° C. or higher. Though the upper limit of the reaction temperature is not particularly restricted, it may be, for example, 160° C. or lower, 140° C. or lower, or 100° C. or lower.

Though the time of the reaction of an amide compound with a hydrazide compound is not particularly restricted, it is usually 0.5 to 150 hours.

It is preferable that the reaction of an amide compound with a hydrazide compound is performed under ordinary pressure (1 atm).

The reaction of an amide compound with a hydrazide compound is preferably performed under an inert gas atmosphere. The inert gas may be, for example, nitrogen, argon or the like.

Suitable embodiments of the present invention have been explained above, but the present invention is not limited to the above-described embodiments.

EXAMPLES

The present invention will be illustrated further in detail by examples below, but the present invention is not limited to these examples.

Measurement of LC-MS was carried out according to the following method.

A measurement sample was dissolved in chloroform or tetrahydrofuran so as to give a concentration of about 2 mg/mL, and about 1 µL of the solution was injected into LC-MS (manufactured by Agilent, trade name: 1100LCMSD). As the mobile phase of LC-MS, acetonitrile and tetrahydrofuran were used while changing the ratio thereof and allowed to flow at a flow rate of 0.2 mL/min. As the column, L-column 2 ODS (3 μm) (manufactured by Chemicals Evaluation and Research Institute, internal diameter: 2.1 mm, length: 100 mm, particle size: 3 μm) was used.

Measurement of NMR was carried out according to the following method.

5 to 10 mg of a measurement sample was dissolved in about 0.5 mL of deuterated chloroform ($CDCl_3$), deuterated tetrahydrofuran, deuterodimethyl sulfoxide, deuterated acetone, deutero-N,N-dimethylformamide, deuterotoluene, deuteromethanol, deuteroethanol, deutero-2-propanol or deuteromethylene chloridehylene, and measurement was performed using an NMR apparatus (manufactured by Agilent, Inc., trade name: INOVA 300 or MERCURY 300).

As the index of the purity of a compound, a value of the high performance liquid chromatography (HPLC) area percentage was used. This value is a value in HPLC (manufactured by Shimadzu Corp., trade name: LC-20A) at 254 nm, unless otherwise stated. In this operation, the compound to be measured was dissolved in tetrahydrofuran or chloroform so as to give a concentration of 0.01 to 0.2 wt %, and depending on the concentration, 1 to 10 of the solution was injected into HPLC. As the mobile phase of HPLC, acetonitrile and tetrahydrofuran were used and allowed to flow at a flow rate of 1 mL/min as gradient analysis of acetonitrile/tetrahydrofuran=100/0 to 0/100 (volume ratio). As the column, Kaseisorb LC ODS 2000 (manufactured by Tokyo Chemical Industry Co., Ltd.) or an ODS column having an equivalent performance was used. As the detector, a photo diode array detector (manufactured by Shimadzu Corp., trade name: SPD-M20A) was used.

As the index of the purity of a compound, the value of gas chromatography (GC) area percentage was used. This value is a value according to GC (manufactured by Agilent, trade name: Agilent7820), unless otherwise stated. In this operation, a compound to be measured was dissolved in tetrahydrofuran or chloroform so as to give a concentration of 0.01 to 0.2% by weight, and the solution was injected in GC in an amount of 1 to 10 μL depending on the concentration. As the carrier, helium gas was used and allowed to flow at a flow rate of 1.0 mL/min. The column oven was used while varying from 50° C. to 300° C. The heater temperature was 280° C. at an injection port and 320° C. at a detector. As the column, BPX-5 manufactured by SGE (30 m 0.25 mm×0.25 μm) was used.

Example 1

According to the following method, a 1,2,4-triazole compound (compound 1) was synthesized.

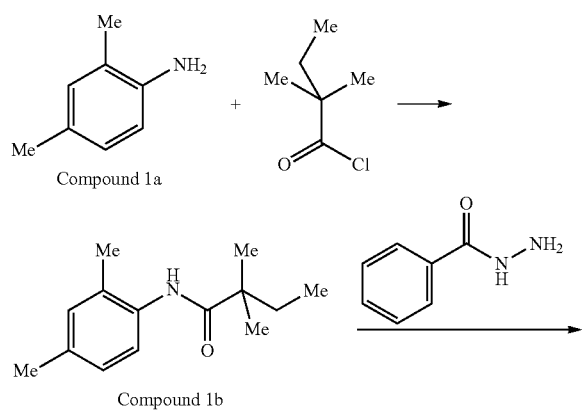

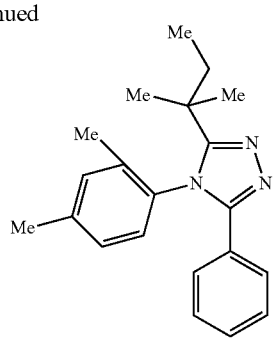

Compound 1

A nitrogen gas atmosphere was prepared in a reaction vessel, then, 2,4-dimethylaniline (20 g) (compound 1a), triethylamine (27 mL) and 275 mL of acetone were added, and the mixture was stirred. Thereafter, the reaction vessel was cooled using an ice bath, and 2,2-dimethylbutyryl chloride (24 mL) was dropped. The mixture was stirred at room temperature for 4 hours, then, ice water was added to the reaction vessel, and the deposited solid was filtrated. The resultant solid was dried at 50° C. under reduced pressure, thereby obtaining a compound 1b (28 g, white solid, yield: 77%). The compound 1b showed a HPLC area percentage value of 99.5%. The above-described operation was repeated, to ensure a necessary amount.

The NMR measurement results of the compound 1b were as described below.

$^1$H-NMR ($CDCl_3$, 400 MHz) δ (ppm): 0.94 (3H, t), 1.29 (6H, s), 1.67 (2H, q), 2.21 (3H, s), 2.28 (3H, s), 6.99 (1H, s), 7.00 (1H, d), 7.12 (1H, br), 7.65 (1H, d).

A nitrogen gas atmosphere was prepared in a reaction vessel, then, the compound 1b (60.0 g), monochlorobenzene (480 mL), 2-fluoropyridine (26 mL) and trifluoromethanesulfonic anhydride (50 mL) were added, and the mixture was stirred at room temperature for 30 minutes. Thereafter, to this was added benzoylhydrazine (41 g), and the mixture was stirred at 90° C. for 3 hours, thereby obtaining a compound 1. A small amount of the reaction liquid was taken out and diluted with chloroform, and the diluted liquid was subjected to HPLC measurement. The yield of the compound 1 determined from HPLC was 97%.

The measurement results of LC-MS and NMR of the compound 1 were as described below.

LC-MS (APCI, positive): [M+H]$^+$ 320.

$^1$H-NMR ($CD_2Cl_2$-$d_2$, 600 MHz) δ (ppm): 7.42-7.37 (m, 2H), 7.35-7.31 (m, 2H), 7.29-7.25 (m, 2H), 7.19 (d, 1H), 7.07 (s, 1H), 2.40 (s, 3H), 1.79-1.72 (m, 4H), 1.57-1.45 (m, 1H), 1.34 (s, 3H), 1.15 (s, 3H), 0.89 (t, 3H).

Comparative Example 1

According to the following method, a 1,2,4-triazole compound (compound 1) was synthesized.

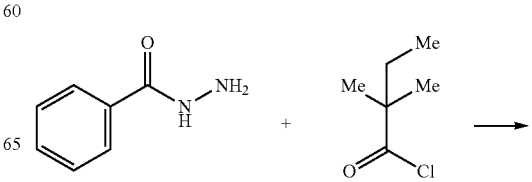

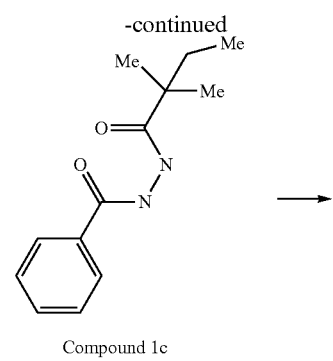

Compound 1c

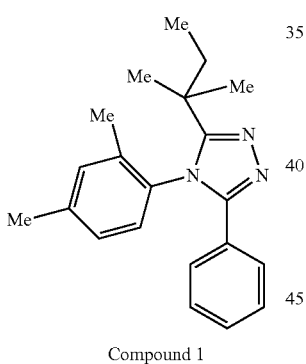

Compound 1d

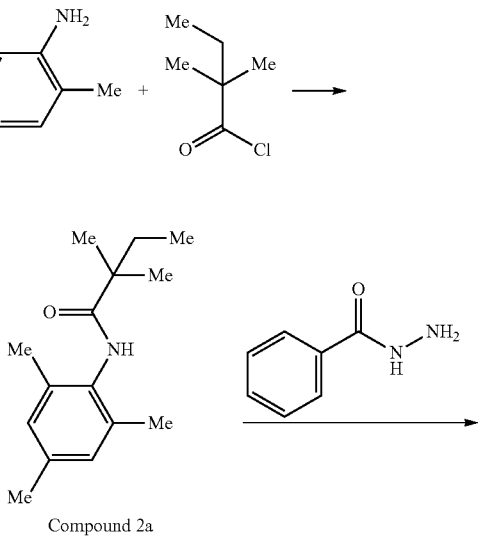

Compound 1

An argon gas atmosphere was prepared in a reaction vessel, then, benzoylhydrazine (25.0 g), triethylamine (28 mL) and tetrahydrofuran (250 mL) were added, and the mixture was stirred.

Thereafter, the reaction vessel was cooled using an ice bath, and 2,2-dimethylbutyryl chloride (22 mL) was dropped. Thereafter, the mixture was stirred at room temperature for 6 hours. The deposited solid was filtrated, the resultant filtrate was concentrated under reduced pressure, and the resultant solid was recrystallized using ethyl acetate, then, the resultant solid was dried at 50° C. under reduced pressure, thereby obtaining a compound 1c (31.5 g, white solid, yield: 73%). The compound 1c showed a HPLC area percentage value of 99.0%.

The NMR measurement results of the compound 1c were as described below.

$^1$H-NMR (CDCl$_3$, 400 MHz) δ (ppm): 0.94 (3H, t), 1.21 (6H, s), 1.62 (2H, q), 7.41 (2H, t), 7.48 (1H, t), 7.88 (2H, d), 8.90 (1H, s), 9.58 (1H, s).

An argon gas atmosphere was prepared in a reaction vessel, then, the compound 1c (2.0 g), tosyl chloride (4.9 g), diisopropylethylamine (3 mL) and acetonitrile (100 mL) were added, and the mixture was stirred at room temperature for 20 hours. An argon gas atmosphere was prepared in a separately prepared reaction vessel, then, 20 mL of a 13% by mass ammonium aqueous solution was added, and the mixture was stirred, and the reaction liquid described above was dropped into the stirring mixture. Thereafter, the mixture was stirred at room temperature for 30 minutes. The resultant reaction liquid was separated, and the resultant organic layer was washed with ion exchanged water. The resultant wash liquid was separated, and the resultant organic layer was dried over magnesium sulfate, then, filtrated, and the resultant filtrate was concentrated under reduced pressure. The resultant solid and hexane were mixed, and the mixture was filtrated, thereby obtaining a compound 1d (1.6 g, white solid, yield: 87%). The compound 1d showed a HPLC area percentage value of 99.5% or more.

The NMR measurement results of the compound 1c were as described below.

$^1$H-NMR (CDCl$_3$, 400 MHz) δ (ppm): 0.86 (3H, t), 1.44 (6H, s), 1.80 (2H, q), 7.48-7.51 (3H, m), 8.03 (2H, d).

An argon gas atmosphere was prepared in a reaction vessel, then, the compound 1d (1.0 g), 2,4-dimethylaniline (1.1 g) and pyridine trifluoroacetate (2 g) were added, and the mixture was stirred at 110° C. for 18 hours, thereby obtaining a compound 1. A small amount of the reaction liquid was taken out and diluted with chloroform, and the diluted liquid was subjected to HPLC measurement. The yield determined from HPLC was 30%.

The measurement result of LC-MS of the compound 1 was as described below.

LC-MS (APCI, positive): [M+H]+ 320.

Example 2

According to the following method, a 1,2,4-triazole compound (compound 2) was synthesized.

Compound 2a

73
-continued

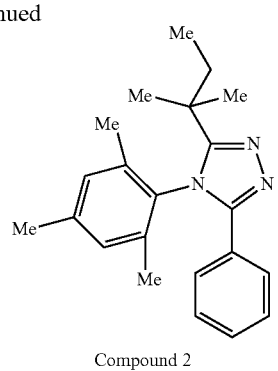

Compound 2

A nitrogen gas atmosphere was prepared in a reaction vessel, then, 2,4,6-trimethylaniline (10 g), triethylamine (22 mL) and 150 mL of chloroform were added, and the mixture was stirred. Thereafter, the reaction vessel was cooled using an ice bath, and 2,2-dimethylbutyryl chloride (9 mL) was dropped. After stirring at room temperature for 1 hour, to the reaction vessel was added a saturated sodium carbonate aqueous solution. The resultant reaction liquid was separated, and the resultant organic layer was washed with ion exchanged water. The resultant wash liquid was separated, the resultant organic layer was dried over magnesium sulfate, then, filtrated, and the resultant filtrate was concentrated, thereby obtaining a white solid. The resultant solid and hexane were mixed, the mixture was filtrated and the resultant solid was dried at 40° C. under reduced pressure, thereby obtaining a compound 2a (14 g, white solid, yield: 80%). The compound 2a showed a HPLC area percentage value of 95.5%.

The NMR measurement results of the compound 2a were as described below.

$^1$H-NMR (CDCl$_3$, 400 MHz) δ (ppm): 0.96 (3H, t), 1.29 (6H, s), 1.68 (2H, q), 2.15 (6H, s), 2.27 (3H, s), 6.87 (2H, s).

An argon gas atmosphere was prepared in a reaction vessel, then, the compound 2a (1.0 g), 2-fluoropyridine (0.5 g), chlorobenzene (10 mL) and trifluoroacetic anhydride (1.3 were added, and the mixture was stirred. Thereafter, the reaction vessel was cooled using a water bath and benzoylhydrazine (0.6 g) was added, and the mixture was stirred at room temperature for 3 hours. A small amount of the resultant reaction liquid was taken out and diluted with chloroform, and the diluted liquid was subjected to HPLC measurement. After confirming that the residual amount of the compound 2a was less than 3%, the reaction liquid was stirred at 90° C. for 3 hours, and stirred at 100° C. for 8 hours, thereby obtaining a compound 2. A small amount of the reaction liquid was taken out and diluted with chloroform, and the diluted liquid was subjected to HPLC measurement. The yield determined from HPLC was 92%.

The measurement result of LC-MS of the compound 2 was as described below.

LC-MS (APCI, positive): [M+H]$^+$ 334.

74

Example 3

According to the following method, a 1,2,4-triazole compound (compound 3) was synthesized.

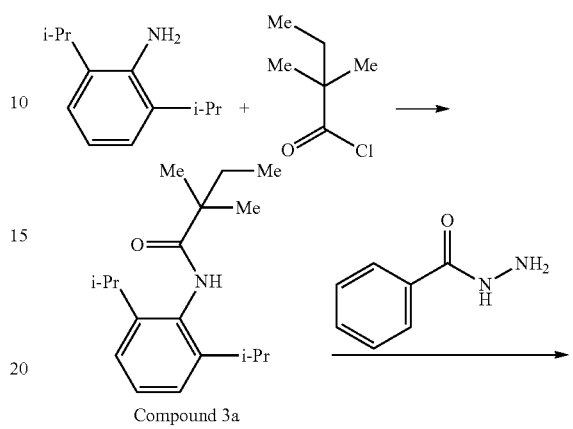

Compound 3a

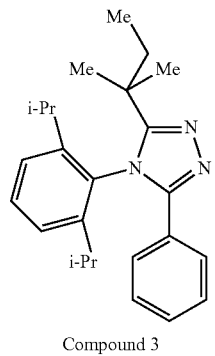

Compound 3

A nitrogen gas atmosphere was prepared in a reaction vessel, then, 2,4-diisopropylaniline (5 g), triethylamine (8 mL) and 75 mL of chloroform were added, and the mixture was stirred. Thereafter, the reaction vessel was cooled using an ice bath, and 2,2-dimethylbutyryl chloride (4 mL) was dropped. After stirring at room temperature for 8 hours, to the reaction vessel was added a saturated sodium carbonate aqueous solution. The resultant reaction liquid was separated, and the resultant organic layer was washed with ion exchanged water. The resultant wash liquid was separated, the resultant organic layer was dried over magnesium sulfate, then, filtrated, and the resultant filtrate was concentrated, thereby obtaining a white solid. The resultant solid and hexane were mixed, the mixture was filtrated and the resultant solid was dried at 50° C. under reduced pressure, thereby obtaining a compound 3a (8 g, white solid). The reaction progressed in a quantitative way. The compound 3a showed a GC area percentage value of 97.9%.

An argon gas atmosphere was prepared in a reaction vessel, then, the compound 3a (1.0 g), 2-fluoropyridine (0.4 g), chlorobenzene (10 mL) and trifluoroacetic anhydride (1.1 g) were added, and the mixture was stirred. Thereafter, the reaction vessel was cooled using a water bath and benzoylhydrazine (0.5 g) was added, and the mixture was stirred at room temperature for 2 hours. A small amount of the resultant reaction liquid was taken out and diluted with chloroform, and the diluted liquid was subjected to HPLC measurement. After confirming that the residual amount of the compound 3a was less than 3%, the reaction liquid was stirred at 90° C. for 5 hours, stirred at 100° C. for 2 hours, stirred at 110° C. for 10 hours and stirred at 120° C. for 5 hours, thereby obtaining a compound 3. A small amount of the reaction liquid was taken out and diluted with chloroform, and the diluted liquid was subjected to HPLC measurement. The yield determined from HPLC was 85%.

The measurement result of LC-MS of the compound 3 was as described below.

LC-MS (APCI, positive): [M+H]$^+$ 376.

Example 4

According to the following method, a 1,2,4-triazole compound (compound 4) was synthesized.

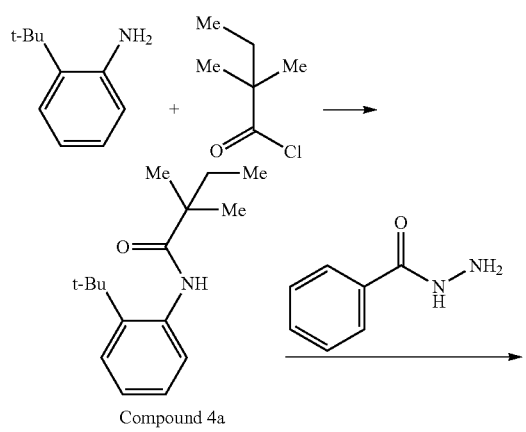

Compound 4a

Compound 4

A nitrogen gas atmosphere was prepared in a reaction vessel, then, 2-tert-butylaniline (3.3 g), triethylamine (7 mL) and 50 mL of chloroform were added, and the mixture was stirred. Thereafter, the reaction vessel was cooled using an ice bath, and 2,2-dimethylbutyryl chloride (3 mL) was dropped. After stirring at room temperature for 6 hours, to the reaction vessel was added a saturated sodium carbonate aqueous solution. The resultant reaction liquid was separated, and the resultant organic layer was washed with ion exchanged water. The resultant wash liquid was separated, and the resultant organic layer was dried over magnesium sulfate, then, filtrated, and the resultant filtrate was concentrated, thereby obtaining a white solid. The resultant solid and hexane were mixed, the mixture was filtrated and the resultant solid was dried at 50° C. under reduced pressure, thereby obtaining a compound 4a (3 g, white solid, yield: 51%). The compound 4a showed a GC area percentage value of 96.2%.

The NMR measurement results of the compound 4a were as described below.

$^1$H-NMR (CDCl$_3$, 400 MHz) δ (ppm): 0.97 (3H, t), 1.30 (6H, s), 1.42 (9H, s), 1.69 (2H, q), 7.14 (1H, t), 7.23 (1H, t), 7.36 (1H, d), 7.67 (1H, d).

An argon gas atmosphere was prepared in a reaction vessel, then, the compound 4a (0.6 g), 2-fluoropyridine (0.3 g), chlorobenzene (6 mL) and trifluoroacetic anhydride (0.8 g) were added, and the mixture was stirred. Thereafter, the reaction vessel was cooled using a water bath and benzoylhydrazine (0.4 g) was added, and the mixture was stirred at room temperature for 1 hour. A small amount of the resultant reaction liquid was taken out and diluted with chloroform, and the diluted liquid was subjected to HPLC measurement. After confirming that the residual amount of the compound 4a was less than 3%, the reaction liquid was stirred at 90° C. for 6 hours and stirred at 100° C. for 6 hours, thereby obtaining a compound 4. A small amount of the reaction liquid was taken out and diluted with chloroform, and the diluted liquid was subjected to HPLC measurement. The yield determined from HPLC was 77%.

The measurement results of LC-MS and NMR of the compound 4 were as described below.

LC-MS (APCI, positive): [M+H]$^+$ 348.

$^1$H-NMR (CDCl$_3$, 400 MHz) δ (ppm): 0.85-0.91 (12H, m), 1.12 (3H, s), 1.33 (3H, s), 1.53-1.63 (1H, m), 1.92-2.02 (1H, m), 7.18-7.32 (6H, m), 7.46-7.50 (3H, m).

Example 5

According to the following method, a 1,2,4-triazole compound (compound 5) was synthesized.

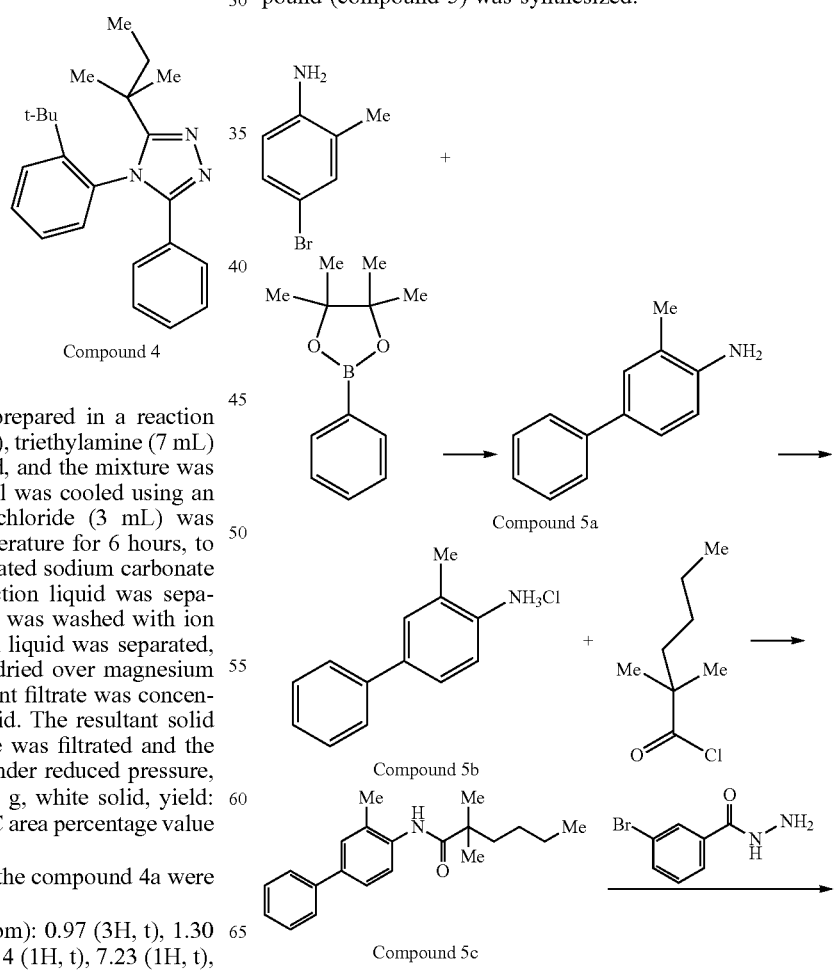

-continued

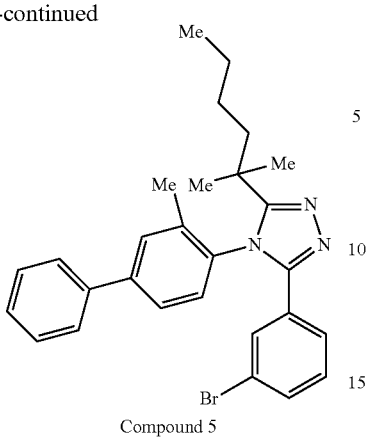

Compound 5

An argon gas atmosphere was prepared in a reaction vessel, then, 2-phenyl-4,4,5,5-tetramethyl-1,3,2-dioxaborolane (50 g), 2-methyl-4-bromoaniline (46 g), tris(dibenzylideneacetone)dipalladium(0) (3 g), 2-dicyclohexylphosphino-2',6'-dimethoxybiphenyl (4 g) and toluene (1 L) were added, and the mixture was stirred at room temperature. Thereafter, a 20% by mass tetraethyl ammonium aqueous solution was dropped into this, and the mixture was stirred at 70° C. for 5 hours. The resultant reaction liquid was cooled down to room temperature, then, separated, and the resultant organic layer was washed with ion exchanged water. The resultant wash liquid was separated, and the resultant organic layer was dried over magnesium sulfate, filtrated, and the resultant filtrate was concentrated. Thereafter, to this were added tetrahydrofuran and activated white earth, and the mixture was stirred at room temperature for 30 minutes, then, filtrated through a filter paved with Celite, and the above-described operation was repeated once again. The resultant filtrate was concentrated under reduced pressure, toluene and activated carbon were added to this, and the mixture was stirred at room temperature for 30 minutes, then, filtrated through a filter paved with Celite, and the resultant filtrate was concentrated. The above-described operation was repeated, thereby obtaining a compound 5a (92 g, reddish brown oil). The compound 5a showed a GC area percentage value of 99.5% or more.

A nitrogen gas atmosphere was prepared in a reaction vessel, then, the compound 5a (92 g) and cyclopentyl methyl ether (214 mL) were added, and the mixture was stirred. Thereafter, the reaction vessel was cooled using an ice bath, and a 16% by mass hydrogen chloride cyclopentyl methyl ether solution (114 g) was dropped, then, n-heptane (649 mL) was dropped. After dropping, the mixture was stirred at room temperature for 1 hour, the deposited solid was filtrated, and the resultant solid was washed with n-heptane and acetone. The resultant solid was recrystallized twice using a mixed solvent of 2-propanol, methanol, ethanol and n-heptane, then, recrystallized once using a mixed solvent of 2-propanol, ethanol and n-heptane, and the resultant solid was dried at room temperature under reduced pressure, to obtain a compound 5b (37 g, pale red solid). The above-described operation was repeated, thereby ensuring a necessary amount of the compound 5b.

The measurement results of NMR of the compound 5b were as described below.

$^1$H-NMR (400 MHz, CDCl$_3$) δ (ppm)=7.33-7.65 (8H, m), 4.85 (3H, s), 2.46 (3H, s).

An argon atmosphere was prepared in a reaction vessel, then, 2,2-dimethylhexanoic acid (29 g), chloroform (174 mL) and N,N-dimethylformamide (0.14 g) were added, and the mixture was stirred at 50° C. Thereafter, thionyl chloride (24 g) was dropped into this, and the mixture was stirred at 50° C. for 4 hours, to generate 2,2-dimethylhexanoyl chloride. A nitrogen gas atmosphere was prepared in a separately prepared reaction vessel, then, the compound 5b (39 g), chloroform (290 mL) and triethylamine (47 mL) were added and the mixture was stirred.

Thereafter, the reaction vessel was cooled using an ice bath, and 2,2-dimethylhexanoyl chloride prepared above was dropped into this. After dropping, the mixture was stirred at room temperature for 2 hours, then, a saturated sodium carbonate aqueous solution (300 mL) was added, and the mixture was stirred at room temperature. The resultant reaction liquid was separated, and the resultant organic layer was washed with a saturated sodium carbonate aqueous solution and ion exchanged water. The resultant wash liquid was separated, and the resultant organic layer was dried over magnesium sulfate, then, filtrated. The resultant filtrate was concentrated under reduced pressure, then, purified by silica gel column chromatography (a mixed solvent of hexane and ethyl acetate), thereby obtaining an oily compound. To the resultant oily compound was added hexane, then, the mixture was stirred for 1 hour while cooling using an acetone bath containing dry ice added, and the resultant solid was filtrated and dried at 50° C. under reduced pressure, thereby obtaining a compound 5c (40 g, white solid, yield: 73%). The compound 5c showed a HPLC area percentage value of 99.5% or more.

The measurement results of NMR of the compound 5c were as described below.

$^1$H-NMR (400 MHz, CDCl$_3$) δ (ppm)=7.98 (1H, d), 7.55 (1H, d), 7.42 (1H, t), 7.41 (4H, m), 7.31 (1H, t), 2.32 (3H, s), 1.62 (2H, s), 1.35 (10H, s), 0.91 (3H, s).

An argon gas atmosphere was prepared in a reaction vessel, then, the compound 5c (30 g), monochlorobenzene (300 mL), 2-fluoropyridine (9 mL) and trifluoromethanesulfonic anhydride (18 mL) were added, and the mixture was stirred at room temperature for 30 minutes. Thereafter, to this was added 2-bromobenzoylhydrazine (23 g). A small amount of the resultant reaction liquid was taken out and diluted with chloroform, and the diluted liquid was subjected to HPLC measurement. After confirming that the residual amount of the compound 5c was less than 3%, the reaction liquid was stirred at 90° C. for 2 hours. A small amount of the resultant reaction liquid was taken out and diluted with chloroform, and the diluted liquid was subjected to HPLC measurement. The yield of the compound 5 determined from HPLC was 97%.

The reaction vessel was cooled, then, to this was added a sodium hydrogen carbonate aqueous solution (300 mL) and the organic layer was extracted, and the resultant organic layer was washed with ion exchanged water. The resultant organic layer was concentrated under reduced pressure, thereby obtaining a solid. To the resultant solid was added hexane and the solid was washed. The washed solid was recrystallized using a mixed solvent of 2-propanol and heptane, and the resultant solid was dried at 50° C. under reduced pressure, thereby obtaining a compound 5 (35 g, isolated yield: 74%) as a white solid. The compound 5 showed a HPLC area percentage value of 99.5% or more.

The measurement results of LC-MS and NMR of the compound 5 were as described below.

LC-MS (APCI, positive): [M+H]$^+$ 488.

$^1$H-NMR (CDCl$_3$, 400 MHz) δ (ppm): 7.57-7.64 (m, 4H), 7.38-7.49 (m, 6H), 7.28-7.30 (d, 1H), 7.07 (t, 1H), 1.85 (3H, s), 1.67-1.74 (2H, m), 1.42-1.50 (1H, m), 1.39 (3H, s), 1.14-1.36 (3H, m), 1.17 (3H, s), 0.88 (3H, t).

Example 6

According to the following method, a 1,2,4-triazole compound (compound 6) was synthesized.

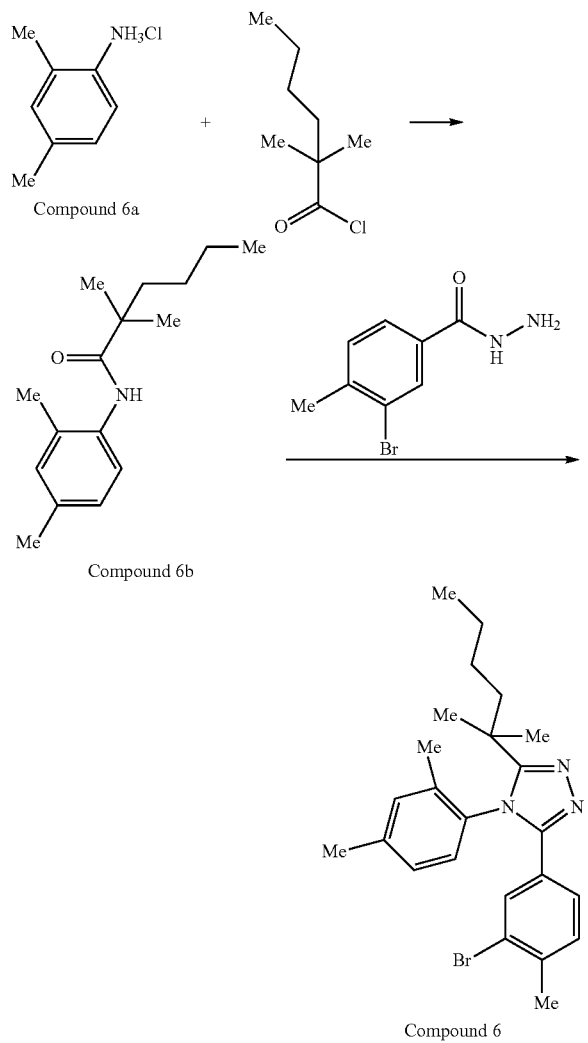

Compound 6a

Compound 6b

Compound 6

An argon gas atmosphere was prepared in a reaction vessel, then, 2,2'-dimethylhexanoic acid (40 g), chloroform (240 mL), N,N'-dimethylformamide (0.21 mL) and thionyl chloride (20 mL) were added, and the mixture was stirred at 45° C. for 3 hours. Thereafter, the reaction vessel was cooled using a water bath, thereby obtaining a reaction liquid containing 2,2'-dimethylhexanoyl chloride. An argon gas atmosphere was prepared in a separately prepared reaction vessel, then, a compound 6a (41.5 g), chloroform (400 mL) and triethylamine (75 mL) were added, and the reaction vessel was placed in an ice bath and cooled. Thereafter, the reaction liquid containing 2,2'-dimethylhexanoyl chloride which is the compound obtained above was dropped into this. After dropping, the mixture was stirred at room temperature for 1 hour, then, a sodium carbonate aqueous solution (2 mol/L, 280 mL) was added, and the mixture was stirred at room temperature. The resultant mixture was separated, thereby obtaining an organic layer. The resultant organic layer was washed with ion exchanged water (280 mL). The resultant organic layer was dried over anhydrous magnesium sulfate, then, concentrated under reduced pressure, thereby obtaining a compound 6b (60 g, yield: 88%) as a pale yellow oil. The compound 6b showed a HPLC area percentage value of 99.5% or more.

The measurement result of TLC-MS of the compound 6b was as described below.

TLC/MS (DART, positive): m/z =248 [M+H]$^+$

An argon gas atmosphere was prepared in a reaction vessel, then, the compound 6b (25.2 g), 2-fluoropyridine (10.8 g), chlorobenzene (202 mL) and trifluoroacetic anhydride (31.3 g) were added, and the mixture was stirred. Thereafter, the reaction vessel was cooled using a water bath, and 2-bromo-3-methylbenzoylhydrazine (25.4 g) was added, and the mixture was stirred at room temperature for 10 minutes. A small amount of the resultant reaction liquid was taken out and diluted with chloroform, and the diluted liquid was subjected to HPLC measurement. After confirming that the residual amount of the compound 6b was less than 2%, the reaction liquid was stirred at 90° C. for 7 hours. A small amount of the resultant reaction liquid was taken out and diluted with chloroform, and the diluted liquid was subjected to HPLC measurement. The yield of the compound 6 determined from HPLC was 91%.

The reaction vessel was cooled, then, to this was added a sodium hydrogen carbonate aqueous solution (100 mL) and an organic layer was extracted, and the resultant organic layer was washed with ion exchanged water. To the resultant organic layer was added magnesium sulfate and the layer was dried, then, 12.6 g of activated carbon was added and the mixture was stirred, and filtrated through a filter paved with Celite, and the resultant filtrate was concentrated under reduced pressure, thereby obtaining a solid. To the resultant solid were added chloroform and tetrahydrofuran, and the mixture was filtrated through a filter paved with silica gel and Celite, and the resultant filtrate was concentrated under reduced pressure, thereby obtaining a solid. The resultant solid was recrystallized using a mixed solvent of toluene and heptane, and the resultant solid was dried at 50° C. under reduced pressure, thereby obtaining a compound 6 (36.2 g, isolated yield: 81%) as a white solid. The compound 6 showed a HPLC area percentage value of 99.5% or more.

The measurement results of NMR of the compound 6 were as described below.

$^1$H-NMR (400 MHz, CD$_2$Cl$_2$-d$_2$) δ=7.61-7.53 (m, 1H), 7.28-7.21 (m, 1H), 7.21-7.12 (m, 1H), 7.12-7.01 (m, 3H), 2.34 (s, 3H), 2.30 (s, 3H), 1.75-1.60 (m, 5H), 1.42-1.08 (m, 10H), 85 (t, 3H).

INDUSTRIAL APPLICABILITY

According to the present invention, a 1,2,4-triazole compound production method capable of obtaining a 1,2,4-triazole compound at high yield with a small number of steps is provided.

The invention claimed is:
1. A production method of a 1,2,4-triazole compound, comprising a step of reacting an amide compound represented by the formula (2) with a hydrazide compound represented by the formula (3) in a solvent in the presence of a Lewis acid and a Lewis base, thereby obtaining a 1,2,4-triazole compound represented by the formula (1):

(2)

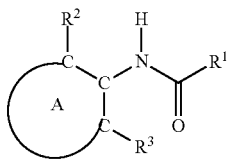

(3)

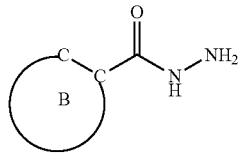

(1)

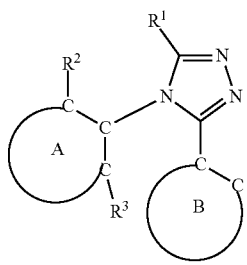

wherein

R¹ represents an alkyl group optionally having a substituent,

R² and R³ each independently represent a hydrogen atom, an alkyl group, a cycloalkyl group, an aryl group, a monovalent heterocyclic group or a substituted amino group and the foregoing groups optionally have a substituent, and R² and R³ may form a ring together with the carbon atoms to which they are attached and the atoms adjacent to the carbon atoms in Ring A, and Ring A and Ring B each independently represent an aromatic hydrocarbon ring or an aromatic heterocyclic ring and the foregoing rings optionally have a substituent, and when a plurality of the substituents are present, they may be the same or different and may be combined together to form a ring together with the atoms to which they are attached.

2. The production method according to claim 1, wherein the amide compound is a compound represented by the formula (2a), and the 1,2,4-triazole compound is a compound represented by the formula (1a):

(2a)

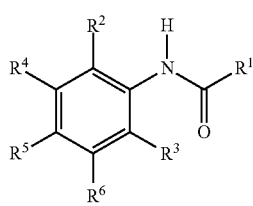

(1a)

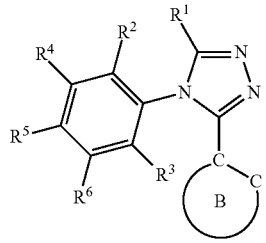

wherein

R¹, R², R³ and Ring B represent the same meaning as described above, and

R⁴, R⁵ and R⁶ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom and the foregoing groups optionally have a substituent, and R² and R⁴, R⁴ and R⁵, R⁵ and R⁶, and R⁶ and R³ each may be combined together to form a ring together with the carbon atoms to which they are attached.

3. The production method according to claim 2, wherein the hydrazide compound is a compound represented by the formula (3a), and the 1,2,4-triazole compound is a compound represented by the formula (1b):

(3a)

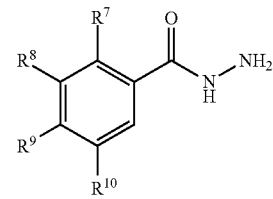

(1b)

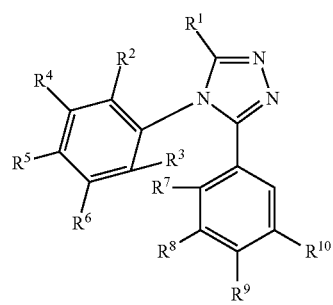

wherein

R¹, R², R³, R⁴, R⁵ and R⁶ represent the same meaning as described above, and

R⁷, R⁸, R⁹ and R¹⁰ each independently represent a hydrogen atom, an alkyl group, a cycloalkyl group, an alkoxy group, a cycloalkoxy group, an aryl group, an aryloxy group, a monovalent heterocyclic group, a substituted amino group or a halogen atom and the foregoing groups optionally have a substituent, and R⁷ and R⁸, R⁸ and R⁹, and R⁹ and R¹⁰ each may be combined together to form a ring together with the carbon atoms to which they are attached.

4. The production method according to claim 1, wherein the Lewis acid is an acid anhydride.

5. The production method according to claim 1, wherein the Lewis base is an organic base.

6. A production method of a 1,2,4-triazole compound, comprising a step of reacting an amide compound represented by the formula (2) with a hydrazide compound represented by the formula (3) in a solvent in the presence of a Lewis acid and a Lewis base at a temperature not higher than the boiling point of the solvent, thereby obtaining a 1,2,4-triazole compound represented by the formula (1):

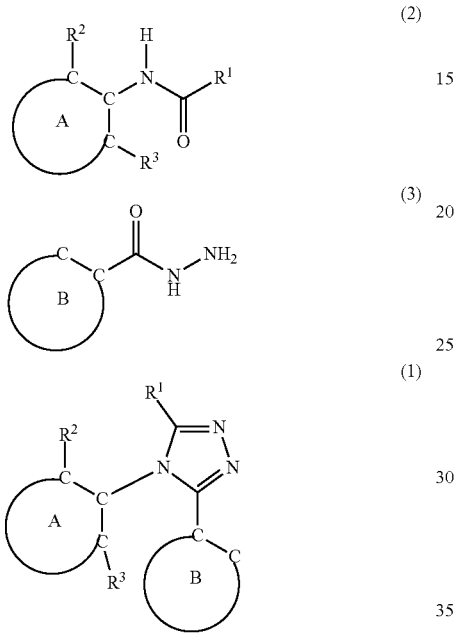

wherein
- $R^1$ represents an alkyl group, a cycloalkyl group, an alkoxy group, a cycloalkoxy group, an aryl group, an aryloxy group, a monovalent heterocyclic group or a substituted amino group and the foregoing groups optionally have a substituent,
- $R^2$ and $R^3$ each independently represent a hydrogen atom, an alkyl group, a cycloalkyl group, an aryl group, a monovalent heterocyclic group or a substituted amino group and the foregoing groups optionally have a substituent, and $R^2$ and $R^3$ may form a ring together with the carbon atoms to which they are attached and the atoms adjacent to the carbon atoms in Ring A, and
- Ring A and Ring B each independently represent an aromatic hydrocarbon ring or an aromatic heterocyclic ring and the foregoing rings optionally have a substituent, and when a plurality of the substituents are present, they may be the same or different and may be combined together to form a ring together with the atoms to which they are attached.

7. The production method according to claim 6, wherein the solvent is a halogenated aromatic hydrocarbon solvent.

8. A production method of a 1,2,4-triazole compound, comprising a step of reacting an amide compound represented by the formula (2) with a hydrazide compound represented by the formula (3) in a solvent in the presence of a Lewis acid and a Lewis base, thereby obtaining a 1,2,4-triazole compound represented by the formula (1):

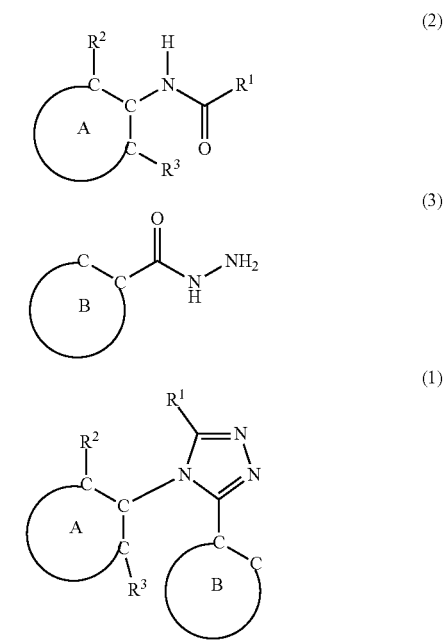

wherein
- $R^1$ represents an alkyl group, a cycloalkyl group, an alkoxy group, a cycloalkoxy group, an aryl group, an aryloxy group, a monovalent heterocyclic group or a substituted amino group and the foregoing groups optionally have a substituent,
- $R^2$ represents an alkyl group, a cycloalkyl group or an aryl group and the foregoing groups optionally have a substituent,
- $R^3$ represents a hydrogen atom, and
- Ring A and Ring B each independently represent an aromatic hydrocarbon ring or an aromatic heterocyclic ring and the foregoing rings optionally have a substituent, and when a plurality of the substituents are present, they may be the same or different and may be combined together to form a ring together with the atoms to which they are attached.

* * * * *